US 010273859B2

(12) United States Patent
Hayashita

(10) Patent No.: US 10,273,859 B2
(45) Date of Patent: Apr. 30, 2019

(54) CONTROL DEVICE OF EXHAUST SENSOR

(71) Applicant: TOYOTA JIDOSHA KABUSHIKI KAISHA, Toyota-shi, Aichi-ken (JP)

(72) Inventor: Go Hayashita, Chigasaki (JP)

(73) Assignee: TOYOTA JIDOSHA KABUSHIKI KAISHA, Toyota-shi (JP)

(*) Notice: Subject to any disclaimer, the term of this patent is extended or adjusted under 35 U.S.C. 154(b) by 166 days.

(21) Appl. No.: 15/619,803

(22) Filed: Jun. 12, 2017

(65) Prior Publication Data

US 2017/0356323 A1 Dec. 14, 2017

(30) Foreign Application Priority Data

Jun. 14, 2016 (JP) .................................. 2016-118391

(51) Int. Cl.
| | |
|---|---|
| *G01M 15/10* | (2006.01) |
| *F01N 11/00* | (2006.01) |
| *G01N 27/416* | (2006.01) |
| *G01N 27/407* | (2006.01) |
| *G01N 27/417* | (2006.01) |

(52) U.S. Cl.
CPC ............ *F01N 11/007* (2013.01); *F01N 11/00* (2013.01); *G01M 15/102* (2013.01); *G01N 27/4075* (2013.01); *G01N 27/4162* (2013.01); *G01N 27/4175* (2013.01); *F01N 2560/025* (2013.01); *F01N 2560/026* (2013.01); *F01N 2560/027* (2013.01); *F01N 2560/20* (2013.01); *Y02T 10/47* (2013.01)

(58) Field of Classification Search
CPC .. F01N 11/007; F01N 11/00; F01N 2560/027; F01N 2560/026; F01N 2560/025; F01N 2560/20; G01N 27/4075; G01N 27/4175; G01N 27/4162; G01M 15/102; Y02T 10/47
USPC ....................................................... 73/114.71
See application file for complete search history.

(56) References Cited

U.S. PATENT DOCUMENTS

| | | | |
|---|---|---|---|
| 6,343,499 B1 | 2/2002 | Inagaki et al. | |
| 8,201,993 B2 * | 6/2012 | Tabery ................ | F02D 41/1494 374/45 |

(Continued)

FOREIGN PATENT DOCUMENTS

| | | |
|---|---|---|
| JP | 2000-193635 A | 7/2000 |
| JP | 2006-322389 A | 11/2006 |
| JP | 2009-529691 A | 8/2009 |

*Primary Examiner* — Freddie Kirkland, III
(74) *Attorney, Agent, or Firm* — Hunton Andrews Kurth LLP

(57) ABSTRACT

A control device of an exhaust sensor comprises a cell temperature detecting part detecting a temperature of the electrochemical cell, a heater control part controlling the heater so that a temperature of the electrochemical cell becomes the target temperature, and a judging part judging whether a water repellency of the protective layer is falling. The judging part judges that the water repellency of the protective layer is falling if a condition for judging abnormality is satisfied. The condition for judging abnormality includes a temperature of the electrochemical cell detected by the cell temperature detecting part falling from the target temperature and a speed of fall of the temperature being faster than a speed of fall of the temperature of the electrochemical cell when the heater is turned off.

16 Claims, 24 Drawing Sheets

(56) References Cited

U.S. PATENT DOCUMENTS

| | | | |
|---|---|---|---|
| 8,479,494 B2* | 7/2013 | Enomoto | F02D 41/1494 |
| | | | 60/274 |
| 8,769,929 B2* | 7/2014 | Weber | B01D 53/30 |
| | | | 60/276 |
| 9,297,791 B2* | 3/2016 | Weiblen | G01N 33/0009 |
| 9,846,110 B2* | 12/2017 | Tylutki | G01N 15/0656 |
| 2009/0116534 A1 | 5/2009 | Tabery et al. | |

* cited by examiner

FIG. 1
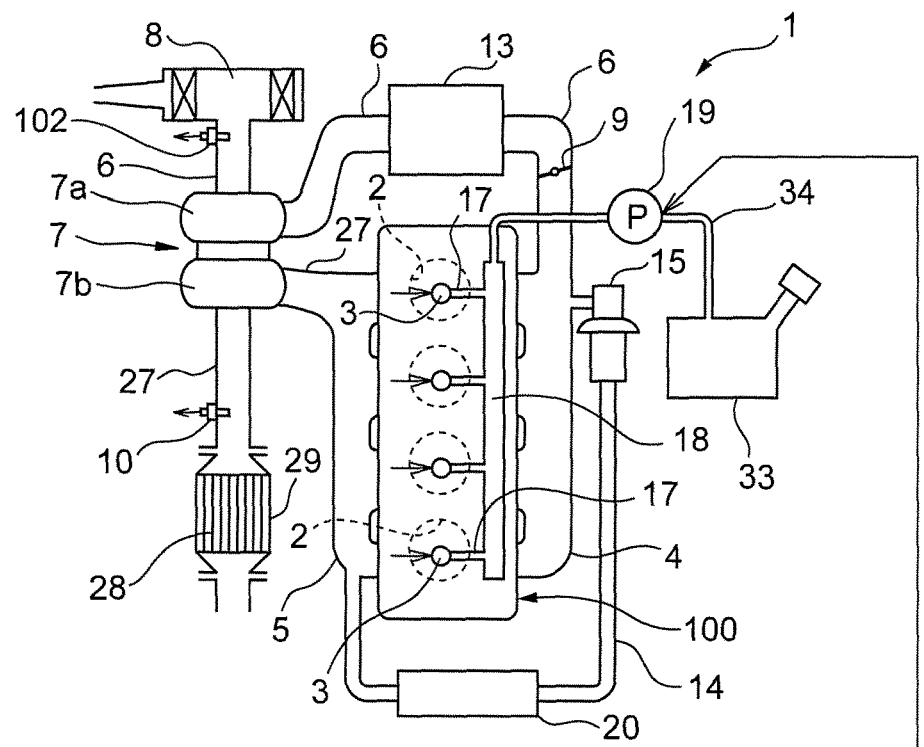
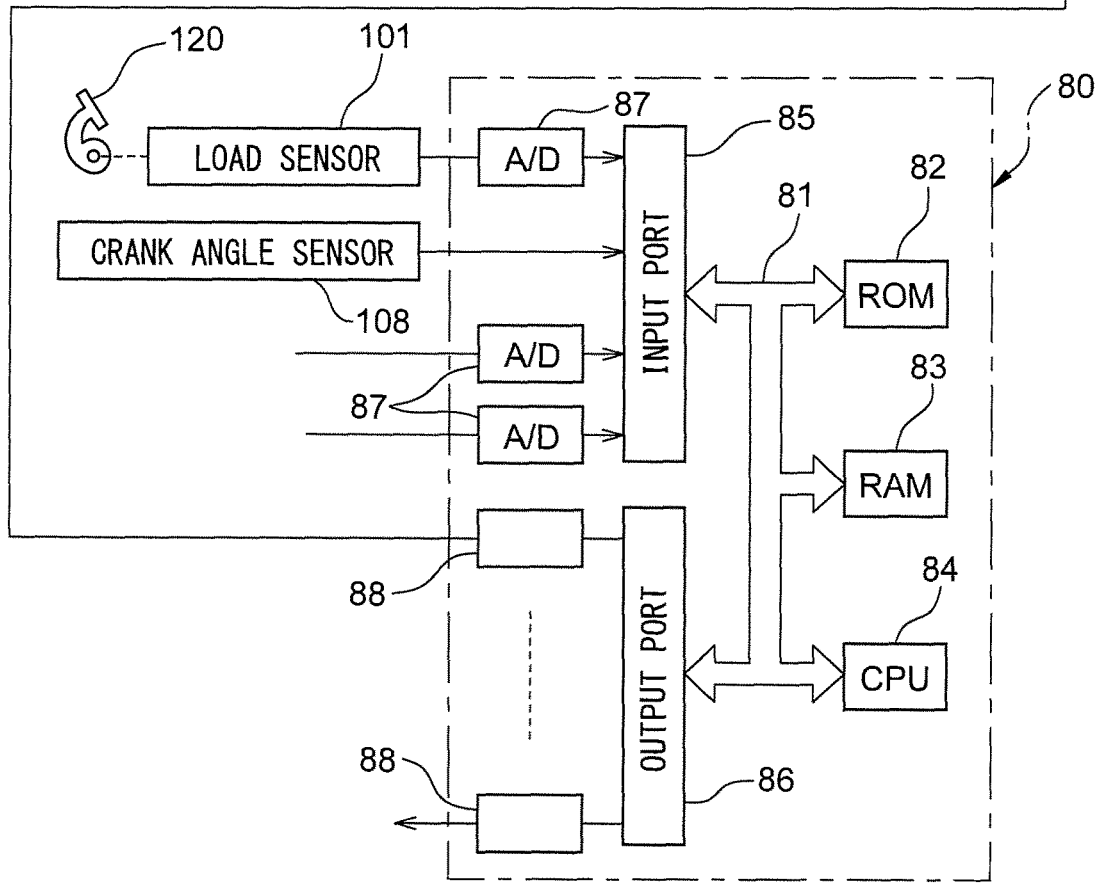

CONTROL DEVICE OF EXHAUST SENSOR

CROSS-REFERENCE TO RELATED APPLICATIONS

The present application claimed priority to Japanese Patent Application No. 2016-118391 filed on Jun. 14, 2016, which is incorporated herein by reference in its entirety.

TECHNICAL FIELD

The present invention relates to a control device of an exhaust sensor.

BACKGROUND ART

It has been known in the past to arrange an exhaust sensor in an exhaust passage of an internal combustion engine to detect a specific component in the exhaust gas (for example, see PLTs 1 to 3). The exhaust sensor described in PLT 1 is provided with an element body provided with an electrochemical cell, and a protective layer formed on the outer surface of the element body and comprised of a porous ceramic. The exhaust sensor is fastened to an exhaust pipe so as to be exposed to exhaust gas. Part of the exhaust gas passes through the protective layer and flows to the inside of the element body. Further, the exhaust sensor is provided with a heater for heating the element body so that the electrochemical cell becomes a predetermined operating temperature or more.

In this regard, when the temperature of the exhaust pipe is the dew point temperature of water or less, the water vapor in the exhaust gas condenses and condensed water is generated. If there is condensed water in the exhaust passage, drops of the condensed water strike the protective layer of the exhaust sensor together with the exhaust gas. If the protective layer does not have water repellency, the drops of water striking the protective layer will penetrate to the inside of the protective layer. If the temperature of the protective layer is high due to heating by the heater, the drops of water penetrating the protective layer will evaporate inside the protective layer. As a result, thermal shock will be given to the protective layer and element body and the element of the exhaust sensor will sometimes crack.

Therefore, PLT 1 describes preventing cracking of the element of the exhaust sensor by utilizing the Leidenfrost phenomenon to give the protective layer of the exhaust sensor water repellency. The "Leidenfrost phenomenon" is the phenomenon where when drops of water strike a high temperature protective layer, a film of water vapor is formed between the protective layer and drops of water whereby transfer of heat between the protective layer and the drops of water is suppressed. If the Leidenfrost phenomenon occurs, the drops of water are repelled from the protective layer, so water is kept from penetrating the protective layer.

CITATION LIST

Patent Literature

PLT 1. Japanese Patent Publication No. 2009-529691A
PLT 2. Japanese Patent Publication No. 2000-193635A
PLT 3. Japanese Patent Publication No. 2006-322389A

SUMMARY OF INVENTION

Technical Problem

However, if soot deposits on the protective layer, the exhaust sensor becomes degraded, etc., the thermal conductivity of the protective layer will fall. As a result, the Leidenfrost phenomenon will become harder to occur, and the water repellency of the protective layer will fall. If the water repellency of the protective layer falls, a part of the drops of water striking the protective layer will penetrate through the protective layer. If the degree of fall of water repellency of the protective layer becomes larger, the amount of water penetrating through the protective layer will increase and the element of the exhaust sensor is liable to crack. Therefore, in order to more reliably prevent the element of the exhaust sensor from cracking due to coverage by water, it is desirable to be able to detect fall in water repellency of the protective layer during operation of the internal combustion engine.

Therefore, an object of the present invention is to provide a control device of an exhaust sensor able to detect a fall in the water repellency of the protective layer of an exhaust sensor during operation of an internal combustion engine.

Solution to Problem

In order to solve the above problem, in a first aspect, there is provided a control device of an exhaust sensor controlling an exhaust sensor arranged in an exhaust passage of an internal combustion engine and detecting a specific component in exhaust gas, wherein the exhaust sensor comprises an element body provided with an electrochemical cell, a protective layer formed on an outer surface of the element body and comprised of a porous ceramic, and a heater heating the element body and the protective layer, the control device comprises a cell temperature detecting part configured to detect a temperature of the electrochemical cell, a heater control part configured to set a target temperature of the electrochemical cell and control the heater so that a temperature of the electrochemical cell becomes the target temperature, and a judging part configured to judge whether a water repellency of the protective layer is falling when the heater control part sets the target temperature to a temperature of a lowest temperature at which a Leidenfrost phenomenon occurs at an outer surface of the protective layer or more, and the judging part is configured to judge that the water repellency of the protective layer is falling if a condition for judging abnormality is satisfied, the condition for judging abnormality including a temperature of the electrochemical cell detected by the cell temperature detecting part falling from the target temperature and a speed of fall of the temperature being faster than a speed of fall of the temperature of the electrochemical cell when the heater is turned off.

In a second aspect, the condition for judging abnormality includes an amount of fall of the temperature of the electrochemical cell from the target temperature being a predetermined amount or more, in the first aspect.

In a third aspect, the condition for judging abnormality includes a temperature of the electrochemical cell falling from the target temperature, then rising to the target temperature, and a time period from when the temperature of the electrochemical cell falls from the target temperature to when it rises to the target temperature being shorter than an ignition period in the internal combustion engine, in the first or second aspect.

In a forth aspect, the condition for judging abnormality includes a temperature of the electrochemical cell falling from the target temperature, then rising to the target temperature, and a speed of fall and a speed of rise of the temperature being a predetermined speed or more, in any one of the first to third aspects.

In a fifth aspect, the condition for judging abnormality includes a temperature of the electrochemical cell falling from the target temperature, then rising to the target temperature, and a speed of fall of the temperature being faster than a speed of rise of the temperature, in any one of the first to fourth aspects.

In a sixth aspect, the control device further comprises an output detecting part configured to detect an output of the exhaust sensor, and the condition for judging abnormality includes an absolute value of the output of the exhaust sensor detected by the output detecting part falling from the value of a predetermined reference value or more when the temperature of the electrochemical cell falling from the target temperature, in any one of the first to fifth aspects.

In a seventh aspect, the condition for judging abnormality includes an amount of fall of the absolute value of the output of the exhaust sensor from the value of the reference value or more being a predetermined amount or more, in the sixth aspect.

In an eighth aspect, the condition for judging abnormality includes the absolute value of the output of the exhaust sensor falling from the value of the reference value or more, then rising to the value of the reference value or more, and a time period from when the absolute value of the output of the exhaust sensor falls from the value of the reference value or more to when it rises to the value of the reference value or more being shorter than an ignition period in the internal combustion engine, in the sixth or seventh aspect.

In a ninth aspect, the condition for judging abnormality includes the absolute value of the output of the exhaust sensor falling from the value of the reference value or more, then rising to the value of the reference value or more, and a speed of fall and speed of rise of the absolute value of the output being a predetermined speed or more, in any one of the sixth to eighth aspects.

In a tenth aspect, the condition for judging abnormality includes the absolute value of the output of the exhaust sensor falling from the value of the reference value or more, then rising to the value of the reference value or more, and a speed of fall of the absolute value of the output being faster than a speed of rise of the absolute value of the output, in any one of the sixth to ninth aspects.

In an eleventh aspect, the control device further comprises an output detecting part configured to detect an output of the exhaust sensor, and the condition for judging abnormality includes the output of the exhaust sensor detected by the output detecting part rising from a value in a predetermined near zero region when the temperature of the electrochemical cell falls, in any one of the first to tenth aspects.

In a twelfth aspect, the condition for judging abnormality includes the output of the exhaust sensor rising from the value in the near zero region then falling to the value in the near zero region, and a time period from when the output of the exhaust sensor rises from the value in the near zero region to when it falls to the value in the near zero region being shorter than an ignition period in the internal combustion engine, in the eleventh aspect.

In a thirteenth aspect, the control device further comprises an exhaust pipe temperature estimating part configured to estimate a temperature of the exhaust pipe around the exhaust sensor, and, the judging part is configured not to judge whether the water repellency of the protective layer is falling after the temperature of the exhaust pipe estimated by the exhaust pipe temperature estimating part reaches a predetermined temperature of a dew point temperature or more, in any one of the first to twelfth aspects.

In a fourteenth aspect, the judging part is configured to judge a degree of fall of the water repellency of the protective layer, and judge that a degree of fall of the water repellency of the protective layer is larger the larger an amount of fall of the temperature of the electrochemical cell from the target temperature when the temperature falls from the target temperature at a speed faster than the speed of fall of the temperature of the electrochemical cell when the heater is turned off, in any one of the first to thirteenth aspects.

In a fifteenth aspect, the heater control part is configured to rise the target temperature when the judging part judges that the water repellency of the protective layer is falling, in any one of the first to fourteenth aspects.

In a sixteenth aspect, the heater control part is configured to rise the target temperature when the judging part judges that the water repellency of the protective layer is falling, and makes an amount of rise of the target temperature larger if a degree of fall of water repellency of the protective layer is relatively large compared with if the degree of fall of water repellency of the protective layer is relatively small, in the fourteenth aspect.

Advantageous Effects of Invention

According to the present invention, there is provided a control device of an exhaust sensor able to detect a fall in the water repellency of the protective layer of an exhaust sensor during operation of an internal combustion engine.

FIG. 1 is a view schematically showing an internal combustion engine in which a control device of an exhaust sensor according to the first embodiment of the present invention is used.

DESCRIPTION OF EMBODIMENTS

Figure 2:
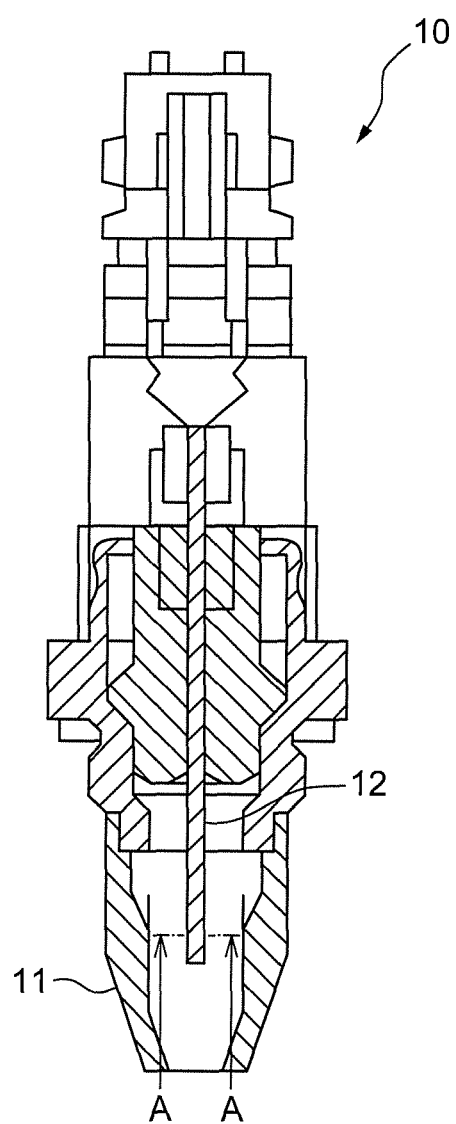
FIG. 2 is an enlarged view of an air-fuel ratio sensor.

Below, referring to the drawings, embodiments of the present invention will be explained in detail. Note that, in the following explanation, similar components will be assigned the same reference notations.

<First Embodiment>

First, referring to FIG. 1 to FIG. 6, a first embodiment of the present invention will be explained.

<Explanation of Internal Combustion Engine as Whole>

FIG. 1 is a view schematically showing an internal combustion engine 1 in which a control device of an exhaust sensor according to the first embodiment of the present invention is used. The internal combustion engine 1 shown in FIG. 1 is a compression ignition type internal combustion engine (diesel engine). The internal combustion engine 1 is for example mounted in a vehicle.

Referring to FIG. 1, the internal combustion engine 1 is provided with an engine body 100, a combustion chamber 2 of each cylinder, an electronically controlled fuel injector 3 injecting fuel into each combustion chamber 2, an intake manifold 4, and an exhaust manifold 5. The intake manifold 4 is connected through an intake pipe 6 to an outlet of a compressor 7a of a turbocharger 7. The inlet of the compressor 7a is connected through the intake pipe 6 to an air cleaner 8. Inside the intake pipe 6, a throttle valve 9 driven by a step motor is arranged. Furthermore, around the intake pipe 6, a cooling device 13 for cooling the intake air flowing through the inside of the intake pipe 6 is arranged. In the internal combustion engine 1 shown in FIG. 1, engine cooling water is guided to the inside of the cooling device 13 and cools the intake air. The intake manifold 4 and intake pipe 6 form an intake passage guiding air to the inside of each combustion chamber 2.

On the other hand, the exhaust manifold 5 is connected through an exhaust pipe 27 to an inlet of a turbine 7b of the turbocharger 7. The outlet of the turbine 7b is connected through the exhaust pipe 27 to a casing 29 housing an exhaust purification catalyst 28. The exhaust manifold 5 and exhaust pipe 27 form an exhaust passage discharging exhaust gas generated by combustion of the air-fuel mixture in each combustion chamber 2. The exhaust purification catalyst 28 is, for example, a selective catalytic reduction type $NO_X$ reduction catalyst (SCR catalyst) or an $NO_X$ storage and reduction catalyst for removing the $NO_X$ in the exhaust gas by reduction. Further, inside the exhaust passage, to reduce particulate matter (PM) in the exhaust gas, an oxidation catalyst, diesel particulate filter (DPF), etc. may be arranged.

The exhaust manifold 5 and the intake manifold 4 are connected through an exhaust gas recirculation (below, referred to as "EGR") passage 14. Inside the EGR passage 14, an electronically controlled EGR control valve 15 is arranged. Further, around the EGR passage 14, an EGR cooling device 20 is arranged for cooling the EGR gas flowing through the inside of the EGR passage 14. In the embodiment shown in FIG. 1, the engine cooling water is guided to the inside of the EGR cooling device 20 and cools the EGR gas.

The fuel is supplied by an electronically controlled variable discharge fuel pump 19 from a fuel tank 33 through a fuel pipe 34 to the inside of a common rail 18. The fuel supplied to the inside of the common rail 18 is supplied through the individual fuel supply pipes 17 to the individual fuel injectors 3.

The various control routines of the internal combustion engine 1 are performed by the electronic control unit (ECU) 80. The ECU 80 is comprised of a digital computer provided with components connected to each other through a bidirectional bus 81 such as a ROM (read only memory) 82, RAM (random access memory) 83, CPU (microprocessor) 84, input port 85, and output port 86. Outputs of a load sensor 101 and an air-flow meter 102 are input through corresponding AD converters 87 to the input port 85. On the other hand, the output port 86 is connected through corresponding drive circuits 88 to the fuel injectors 3, throttle valve drive step motor, EGR control valve 15, and fuel pump 19.

The load sensor 101 generates an output voltage proportional to an amount of depression of an accelerator pedal 120. Therefore, the load sensor 101 detects the engine load. The air-flow meter 102 is arranged inside the intake passage between the air cleaner 8 and compressor 7a and detects the amount of air flowing through the inside of the intake pipe 6. Furthermore, a crank angle sensor 108 generating an output pulse every time the crankshaft rotates by for example 15° is connected to the input port 85. The crank angle sensor 108 5s used to detect the engine speed.

Note that, the internal combustion engine 1 may be a spark ignition type internal combustion engine with spark plugs arranged in the combustion chambers. Further, specific configurations of the internal combustion engine 1 such as the cylinder array, configuration of the intake and exhaust systems, and presence or absence of a turbocharger may differ from the configuration shown in FIG. 1.

<Explanation of Air-Fuel Ratio Sensor>

In the present embodiment, as the exhaust sensor controlled by the control device of an exhaust sensor, an air-fuel ratio sensor 10 is arranged at the exhaust passage of the internal combustion engine 1. The air-fuel ratio sensor 10 detects a specific component in the exhaust gas flowing through the exhaust passage of the internal combustion engine 1. Specifically, the air-fuel ratio sensor 10 detects the concentration of oxygen in the exhaust gas to thereby linearly detect the air-fuel ratio of the exhaust gas.

In the present embodiment, the air-fuel ratio sensor 10 is arranged in the exhaust passage at the upstream side of the exhaust purification catalyst 28 in the direction of flow of exhaust gas. Note that, the air-fuel ratio sensor 10 may be arranged at another position in the exhaust passage, for example, at the downstream side of the exhaust purification catalyst 28 in the direction of flow of exhaust gas.

Below, referring to FIG. 2 and FIG. 3, the configuration of the air-fuel ratio sensor 10 will be explained. FIG. 2 is an enlarged view of the air-fuel ratio sensor 10. In FIG. 2, the front end side of the air-fuel ratio sensor 10 is shown by a cross-sectional view. The air-fuel ratio sensor 10 is fastened to the exhaust pipe 27 in the state with the front end part 11 inserted inside the exhaust pipe 27. The air-fuel ratio sensor 10 is provided with a sensor element 12 having a plate-like shape at its inside.

Figure 3:
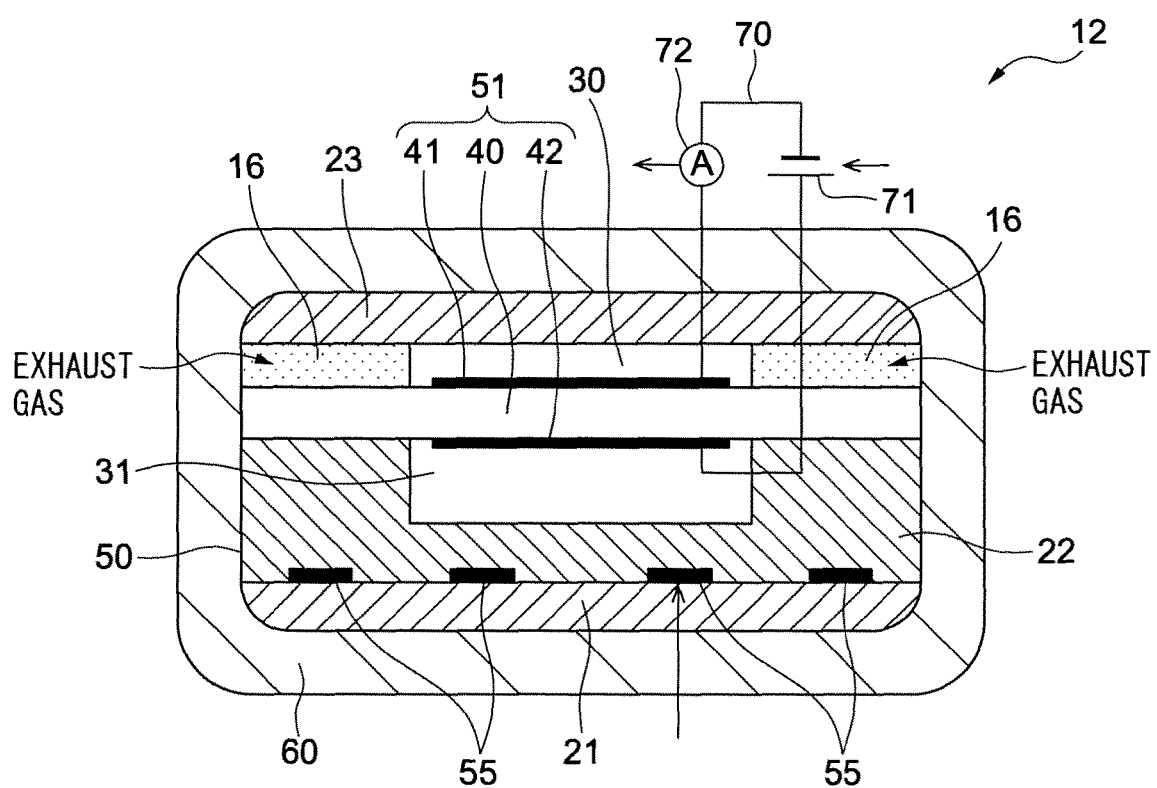
FIG. 3 is a cross-sectional view of a sensor element of an air-fuel ratio sensor along the line A-A of FIG. 2.

FIG. 3 is a cross-sectional view of a sensor element 12 of the air-fuel ratio sensor 10 along the line A-A of FIG. 2. As shown in FIG. 3, the sensor element 12 of the air-fuel ratio sensor 10 is provided with an element body 50 provided with a sensor cell 51 and a protective layer 60 formed on the outer surface of the element body 50.

The element body 50 is provided with a measured gas chamber 30 and a reference gas chamber 31. When the air-fuel ratio sensor 10 is arranged in the exhaust passage of the internal combustion engine 1, exhaust gas flowing through the exhaust passage is introduced into the measured gas chamber 30 as the measured gas. Reference gas is introduced into the reference gas chamber 31. The reference gas is for example the atmosphere. In this case, the reference gas chamber 31 is opened to the atmosphere.

The air-fuel ratio sensor 10 is a laminate type air-fuel ratio sensor comprised of a plurality of layers laminated together. The element body 50 is provided with a solid electrolyte layer 40, diffusion regulating layer 16, first barrier layer 21, second barrier layer 22, and third barrier layer 23. The solid electrolyte layer 40 is a thin plate member having oxide ion conductivity. The solid electrolyte layer 40 is, for example, a sintered body of $ZrO_2$ (zirconia), $HfO_2$, $ThO_2$, $Bi_2O_3$, etc. to which CaO, MgO, $Y_2O_3$, $Yb_2O_3$, etc. is added as a stabilizer. The diffusion regulating layer 16 is a thin plate member having gas permeability. The diffusion regulating layer 16 is, for example, comprised of alumina, magnesia, silica, spinel, mullite, or other porous ceramic. The barrier layers 21 to 23 are gas barrier type thin sheet members, and, for example, include alumina.

The layers of the element body 50 are comprised of, from the bottom of FIG. 3, the first barrier layer 21, second barrier layer 22, solid electrolyte layer 40, diffusion regulating layer 16, and third barrier layer 23 stacked in that order. The measured gas chamber 30 is formed and defined by the solid electrolyte layer 40, diffusion regulating layer 16, and third barrier layer 23. The exhaust gas passes through the protective layer 60 and diffusion regulating layer 16 and is introduced to the inside of the measured gas chamber 30.

The diffusion regulating layer 16 regulates the diffusion of the measured gas. Note that, the measured gas chamber 30 may be configured in any form so long as adjoining the solid electrolyte layer 40 and having the measured gas introduced into it.

The reference gas chamber 31 is formed and defined by the solid electrolyte layer 40 and the second barrier layer 22. Note that, the reference gas chamber 31 may be configured in any form so long as adjoining the solid electrolyte layer 40 and having the reference gas flow into it.

The sensor cell 51 is an electrochemical cell having a solid electrolyte layer 40, first electrode 41, and second electrode 42. The first electrode 41 is arranged on the surface of the solid electrolyte layer 40 on the measured gas chamber 30 side so that it is exposed to the measured gas of the measured gas chamber 30. On the other hand, the second electrode 42 is arranged on the surface of the solid electrolyte layer 40 on the reference gas chamber 31 side so that it is exposed to the reference gas inside the reference gas chamber 31. The first electrode 41 and the second electrode 42 are arranged so as to face each other across the solid electrolyte layer 40. The first electrode 41 and second electrode 42 are comprised of platinum (Pt) or another precious metal with a high catalytic activity. For example, the first electrode 41 and second electrode 42 are porous cermet electrodes including mainly Pt.

The protective layer 60 is formed on the outer surface of the element body 50 so as to cover the entire outer surface of the element body 50. The protective layer 60 has a gas permeability and is comprised of alumina, titania, zirconia, silicon carbide, silicon nitride, zinc oxide, and other porous ceramic.

The sensor element 12 is further provided with a heater 55. In the present embodiment, the heater 55, as shown in FIG. 3, is arranged between the first barrier layer 21 and the second barrier layer 22. The heater 55 is, for example, a thin plate member of cermet including platinum (Pt) and ceramic (for example, alumina etc.) and forms a heat generating element generating heat by conduction of current. The heater 55 heats the element body 50 and protective layer 60.

The first electrode 41 and second electrode 42 of the sensor cell 51 are connected to an electrical circuit 70. The electrical circuit 70 is provided with a power supply 71 and current detector 72. The power supply 71 applies voltage across the electrodes so that the potential of the second electrode 42 becomes higher than the potential of the first electrode 41. The output port 86 of the ECU 80 is connected through a corresponding drive circuit 88 to the power supply 71. Therefore, the ECU 80 can control the power supply 71 and control the voltage applied to the sensor cell 51. Further, the current detector 72 detects the current flowing through the sensor cell 51 as the output of the sensor cell 51. The output of the current detector 72 is input through the corresponding AD converter 87 to the input port 85 of the ECU 80. Therefore, the ECU 80 can acquire the output of the sensor cell 51 detected by the current detector 72 from the current detector 72.

The air-fuel ratio sensor 10 detects the limit current flowing through the sensor cell 51 when applying predetermined voltage to the sensor cell 51 so as to detect the air-fuel ratio of the exhaust gas. Therefore, the air-fuel ratio sensor 10 in the present embodiment is a so-called limit current type air-fuel ratio sensor.

<Leidenfrost Phenomenon>

In this regard, when the temperature of the exhaust pipe 27 is the dew point temperature of water or less, the water vapor in the exhaust gas condenses and condensed water is formed. If there is condensed water in the exhaust passage, the drops of the condensed water strike the protective layer 60 of the air-fuel ratio sensor 10 together with the exhaust gas. When the protective layer 60 does not have water repellency, the drops of water striking the protective layer 60 penetrate to the inside of the protective layer 60. When due to heating by the heater 55, the temperature of the protective layer 60 is high, the drops of water penetrating to the protective layer 60 evaporate inside the protective layer 60. As a result, the protective layer 60 and element body 50 are given thermal shock and the element of the air-fuel ratio sensor 10 sometimes cracks.

The protective layer 60 has water repellency when the temperature is high. This property is obtained by causing the Leidenfrost phenomenon. The "Leidenfrost phenomenon" is the phenomenon where when drops of water strike a high temperature protective layer 60, a film of water vapor is formed between the protective layer 60 and drops of water whereby transfer of heat between the protective layer 60 and the drops of water is suppressed. If the Leidenfrost phenomenon occurs, the drops of water are repelled from the protective layer 60, so water is kept from penetrating the protective layer 60.

<Drop in Water Repellency of Protective Layer>

Figure 4:
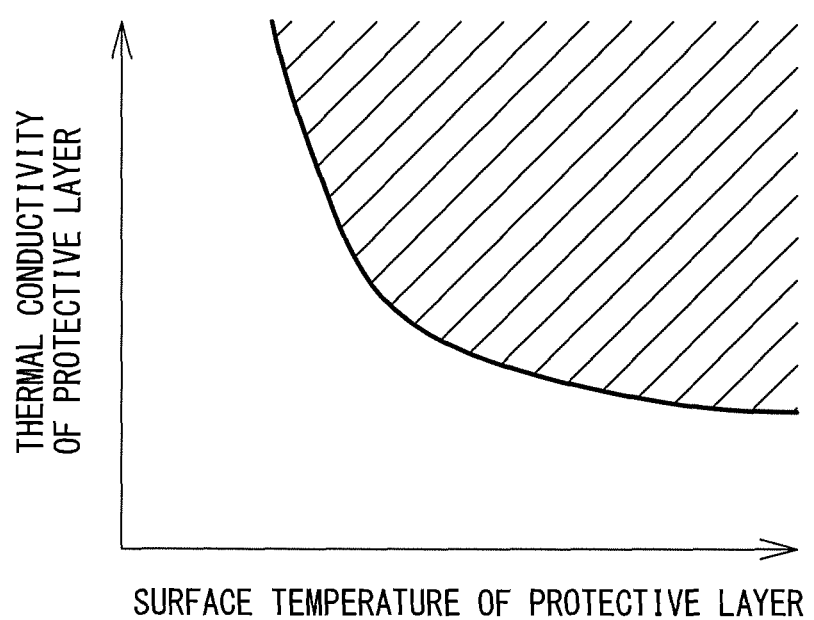
FIG. 4 is a graph showing a region where the Leidenfrost phenomenon occurs when changing a surface temperature and thermal conductivity of a protective layer.

However, if soot deposits on the protective layer 60, the air-fuel ratio sensor 10 deteriorates, etc., the thermal conductivity of the protective layer 60 will fall. FIG. 4 is a graph showing a region where the Leidenfrost phenomenon occurs when changing the surface temperature and thermal conductivity of the protective layer 60. In FIG. 4, the region where the Leidenfrost phenomenon occurs is shown by hatching.

As shown in FIG. 4, if the thermal conductivity of the protective layer 60 falls, the Leidenfrost phenomenon will become harder to occur and the temperature required for causing the Leidenfrost phenomenon will rise. That is, if the thermal conductivity of the protective layer 60 falls, the water repellency of the protective layer 60 will fall. If the water repellency of the protective layer 60 falls, part of the drops of water striking the protective layer 60 will penetrate through the protective layer 60. If the degree of fall of the water repellency of the protective layer 60 becomes larger, the amount of water penetrating through the protective layer 60 will increase, so the element of the air-fuel ratio sensor 10 is liable to crack. Therefore, in order to more reliably prevent the element of the exhaust sensor 10 from cracking due to coverage by water, it is desirable to be able to detect fall in water repellency of the protective layer 60 during operation of the internal combustion engine 1.

<Explanation of Control Device of Exhaust Sensor>

Figure 5:
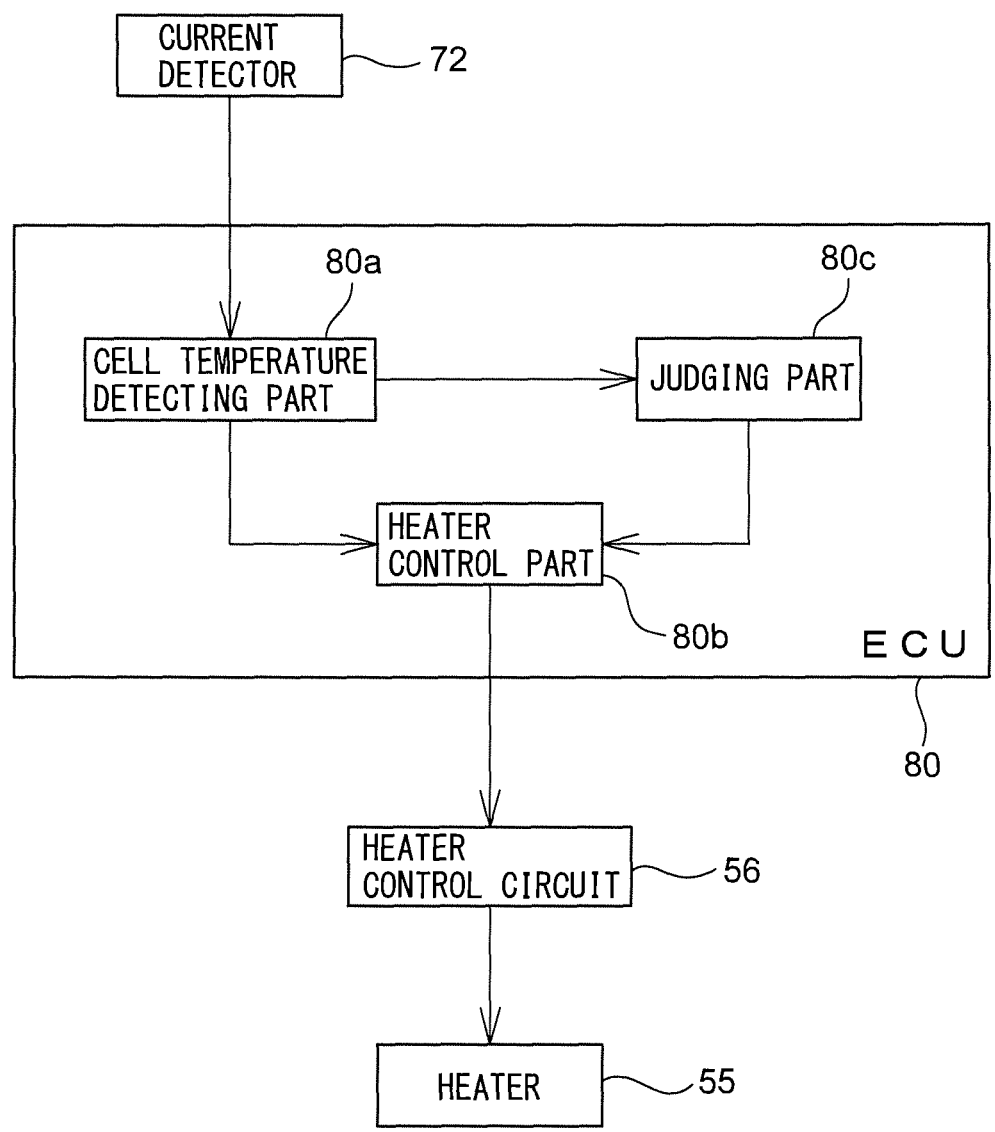
FIG. 5 is a block diagram schematically showing the configuration of a control device of an exhaust sensor, etc., according to the first embodiment of the present invention.

Therefore, the control device of an exhaust sensor according to the present embodiment performs the following control at the time of the startup of the internal combustion engine 1 so as to detect fall in water repellency of the protective layer 60. FIG. 5 is a block diagram schematically showing the configuration of a control device of an exhaust sensor according to a first embodiment of the present invention. The control device of an exhaust sensor is provided with a cell temperature detecting part 80a, a heater control part 80b, and a judging part 80c. In the present embodiment, the cell temperature detecting part 80a, the heater control part 80b, and the judging part 80c are parts of the ECU 80.

The cell temperature detecting part 80a detects the temperature of the sensor cell 51. Specifically, the cell temperature detecting part 80a calculates the temperature of the sensor cell 51 based on an impedance of the sensor cell 51.

The cell temperature detecting part 80a calculates the impedance of the sensor cell 51 based on the output of the sensor cell 51 detected by the current detector 72 when high frequency voltage is applied from the power supply 71 to the sensor cell 51. Note that, the cell temperature detecting part 80a may calculate the temperature of the sensor cell 51 based on an interelectrode resistance of the sensor cell 51. Further, when the inside of the exhaust sensor (in the present embodiment, air-fuel ratio sensor 10) is provided with a thermocouple, the cell temperature detecting part 80a may use the thermocouple to detect the temperature of the sensor cell 51.

The heater control part 80b sets the target temperature of the sensor cell 51 and controls the heater 55 so that the temperature of the sensor cell 51 becomes the target temperature. The heater control part 80b controls the heater 55 through the heater control circuit 56. Specifically, the heater control part 80b controls by feedback the power supplied to the heater 55 through the heater control circuit 56 so that the temperature of the sensor cell 51 detected by the cell temperature detecting part 80a becomes the target temperature. When the sensor cell 51 is heated by the heater 55, the protective layer 60 is also similarly heated by the heater 55. For this reason, the temperature of the protective layer 60 is correlated with the temperature of the sensor cell 51. Therefore, due to the above-mentioned feedback control, the heater control part 80b can control not only the temperature of the sensor cell 51 but also the temperature of the protective layer 60.

The heater control part 80b sets the target temperature of the sensor cell 51 to a temperature of the lowest temperature at which the Leidenfrost phenomenon occurs at the outer surface of the protective layer 60 or more so as to prevent the element of the air-fuel ratio sensor 10 from cracking due to coverage by water at the time of startup of the internal combustion engine 1 or after startup. The judging part 80c judges whether the water repellency of the protective layer 60 is falling when the heater control part 80b sets the target temperature to a temperature of lowest temperature at which the Leidenfrost phenomenon occurs at the outer surface of the protective layer 60 or more. The "lowest temperature at which the Leidenfrost phenomenon occurs at the outer surface of the protective layer 60" is the lower limit value of the temperature at which the Leidenfrost phenomenon occurs when an extremely small amount of drops of water strike the protective layer 60 and, for example, is 400° C.

The judging part 80c judges that the water repellency of the protective layer 60 is falling when the condition for judging abnormality is satisfied. If the water repellency of the protective layer 60 falls, part of the water striking the protective layer 60 penetrates through the protective layer 60 and the temperature of the protective layer 60 and sensor cell 51 falls. Further, the speed of fall of the temperature of the sensor cell 51 at this time is faster than the speed of fall of the temperature of the sensor cell 51 when turning the heater 55 off. For this reason, in the present embodiment, the condition for judging abnormality includes the temperature of the sensor cell 51 detected by the cell temperature detecting part 80a falling from the target temperature and the speed of fall of the temperature of the sensor cell 51 at this time being faster than the speed of fall of the temperature of the sensor cell 51 when turning the heater 55 off. The speed of fall of the temperature of the sensor cell 51 when turning the heater 55 off is determined in advance by experiments or calculations. Note that, the "speed of fall of temperature" means the amount of fall in temperature per unit time.

The control device of an exhaust sensor in the present embodiment can detect a fall in the water repellency of the protective layer 60 of the air-fuel ratio sensor 10 during operation of internal combustion engine 1 by performing the above control.

<Control Routine of Processing for Judging Abnormality>

Figure 6:
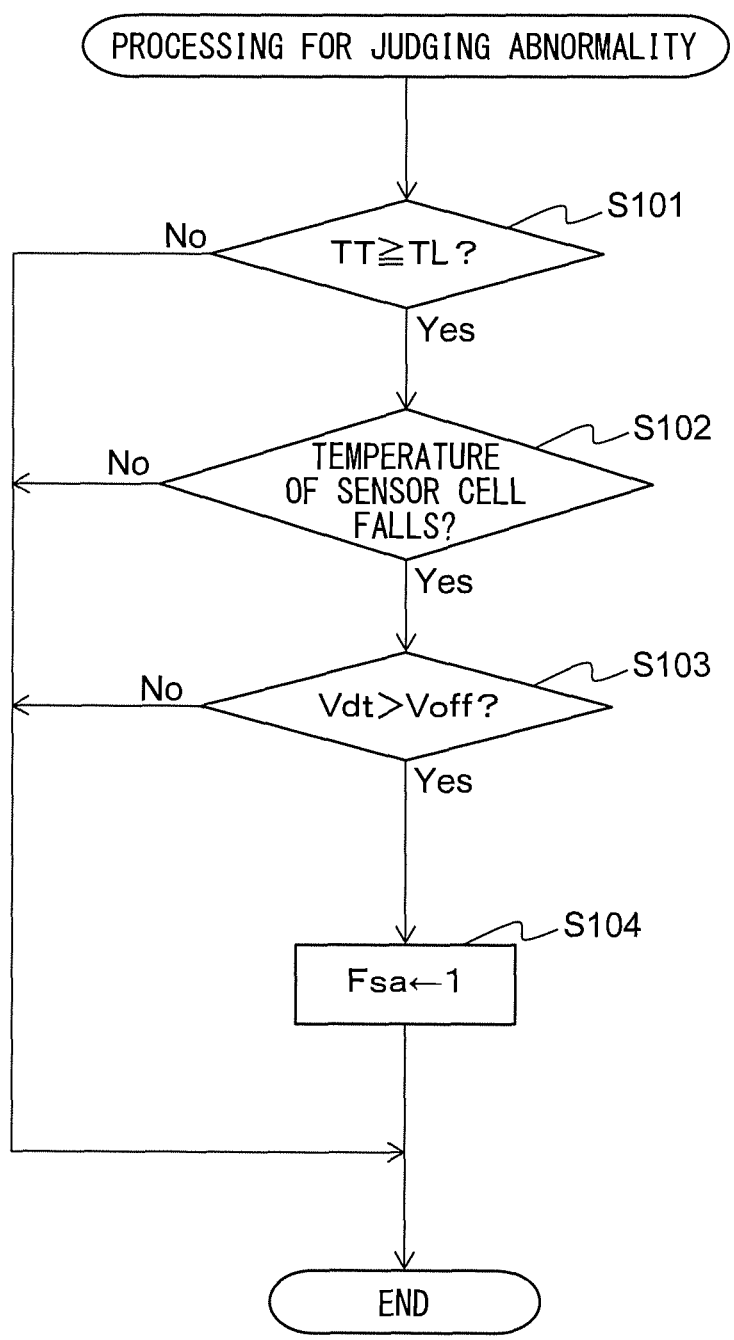
FIG. 6 is a flow chart showing a control routine of processing for judging abnormality in the first embodiment of the present invention.

Below, referring to the flow chart of FIG. 6, control for judging a fall in the water repellency of the protective layer 60 will be explained in detail. FIG. 6 is a flow chart showing a control routine of processing for judging abnormality in the first embodiment of the present invention. The illustrated control routine is repeatedly performed by the ECU 80 at predetermined time intervals after the startup of the internal combustion engine 1.

First, at step S101, the judging part 80c judges whether the target temperature TT of the sensor cell 51 set by the heater control part 80b is a temperature of the lowest temperature TL at which the Leidenfrost phenomenon occurs at the outer surface of the protective layer 60 or more. The lowest temperature TL is for example 400° C.

When it is judged at step S101 that the target temperature TT is less than the lowest temperature TL, the present control routine is ended. In this case, it is not judged whether the water repellency of the protective layer 60 is falling. On the other hand, when it is judged at step S101 that the target temperature TT is the lowest temperature TL or more, the present control routine proceeds to step S102.

At step S102, the judging part 80c judges whether the temperature of the sensor cell 51 is falling from the target temperature TT. The temperature of the sensor cell 51 is detected by the cell temperature detecting part 80a. If it is judged at step S102 that the temperature of the sensor cell 51 is falling from the target temperature TT, the present control routine proceeds to step S103.

At step S103 the judging part 80c judges whether the speed of fall Vdt of the temperature of the sensor cell 51 is faster than the speed of fall Voff of the temperature of the sensor cell 51 when turning the heater 55 off. The speed of fall Vdt is detected by the cell temperature detecting part 80a. The speed of fall Voff of the temperature of the sensor cell 51 when turning the heater 55 off is determined in advance by experiments or calculations. If it is judged at step S103 that the speed of fall Vdt is faster than the speed of fall Voff, the present control routine proceeds to step S104.

At step S104, the judging part 80c judges that the water repellency of the protective layer 60 is falling and sets the sensor abnormality flag Fsa to "1". The initial value of the sensor abnormality flag Fsa is zero. Further, the sensor abnormality flag Fsa is made zero when the ignition switch of the vehicle carrying the internal combustion engine 1 is turned off or when the internal combustion engine 1 is stopped. After step S104, the present control routine is ended.

On the other hand, if it is judged at step S102 that the temperature of the sensor cell 51 has not fallen from the target temperature TT or if it is judged at step S103 that the speed of fall Vdt is the speed of fall Voff or less, the present control routine is ended.

<Second Embodiment>

The configuration and control of the control device of an exhaust sensor according to a second embodiment are basically similar to the configuration and control of the control device of an exhaust sensor according to the first embodiment except for the points explained below. For this reason, below, the second embodiment of the present invention will be explained centered on the parts different from the first embodiment.

If the protective layer 60 is covered by water when the water repellency of the protective layer 60 is falling and the temperature of the sensor cell 51 falls from the target temperature, the amount of fall of the temperature of the sensor cell 51 from the target temperature becomes a predetermined amount or more. For this reason, in the second embodiment, the condition for judging abnormality includes the amount of fall of the temperature of the sensor cell 51 from the target temperature being a predetermined amount or more. The predetermined amount is determined in advance by experiments or calculations and is for example 15° C. In the second embodiment, it is possible to suppress misjudging that the water repellency of the protective layer 60 is falling by detecting change of the temperature of the sensor cell 51 due to factors other than coverage by water, so it is possible to more precisely detect a fall in the water repellency of the protective layer 60.

Figure 7:
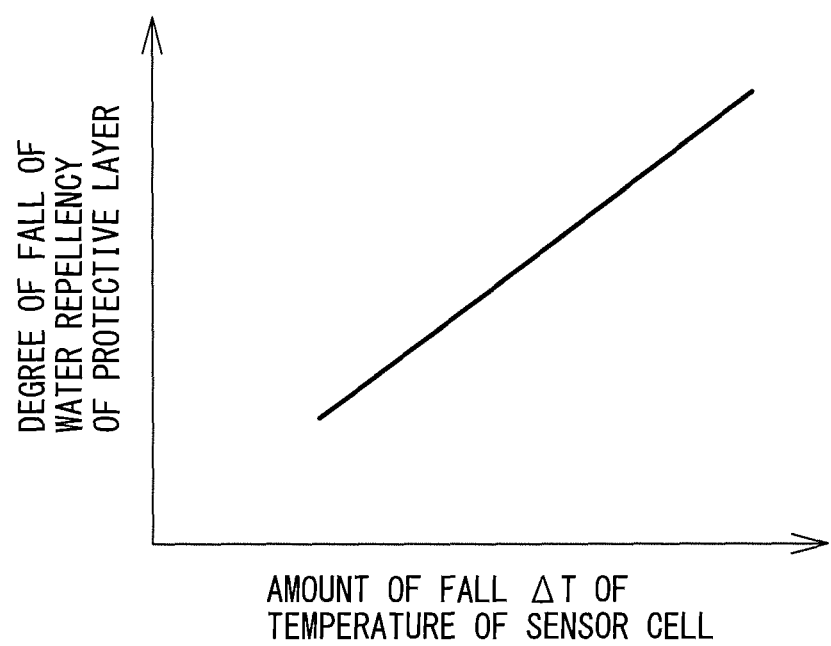
FIG. 7 is a map showing the relationship between an amount of fall in temperature of a sensor cell and a degree of fall of water repellency of the protective layer.

Further, in the second embodiment, the judging part 80c judges the degree of fall of the water repellency of the protective layer 60. The judging part 80c judges the degree of fall of the water repellency of the protective layer 60 to be larger the larger the amount of fall of the temperature of the sensor cell 51 from the target temperature when the temperature of the sensor cell 51 falls from the target temperature at a speed faster than the speed of fall of the temperature of the sensor cell 51 when turning the heater 55 off. The judging part 80c uses a map such as shown in FIG. 7 to calculate the degree of fall of the water repellency of the protective layer 60. In this map, the degree of fall of the water repellency of the protective layer 60 is shown as a function of the amount of fall in temperature ΔT of the sensor cell 51. By judging the degree of fall of the water repellency of the protective layer 60, it becomes possible to control the exhaust sensor according to the degree of fall of the water repellency.

<Control Routine of Processing for Judging Abnormality>

Figure 8:
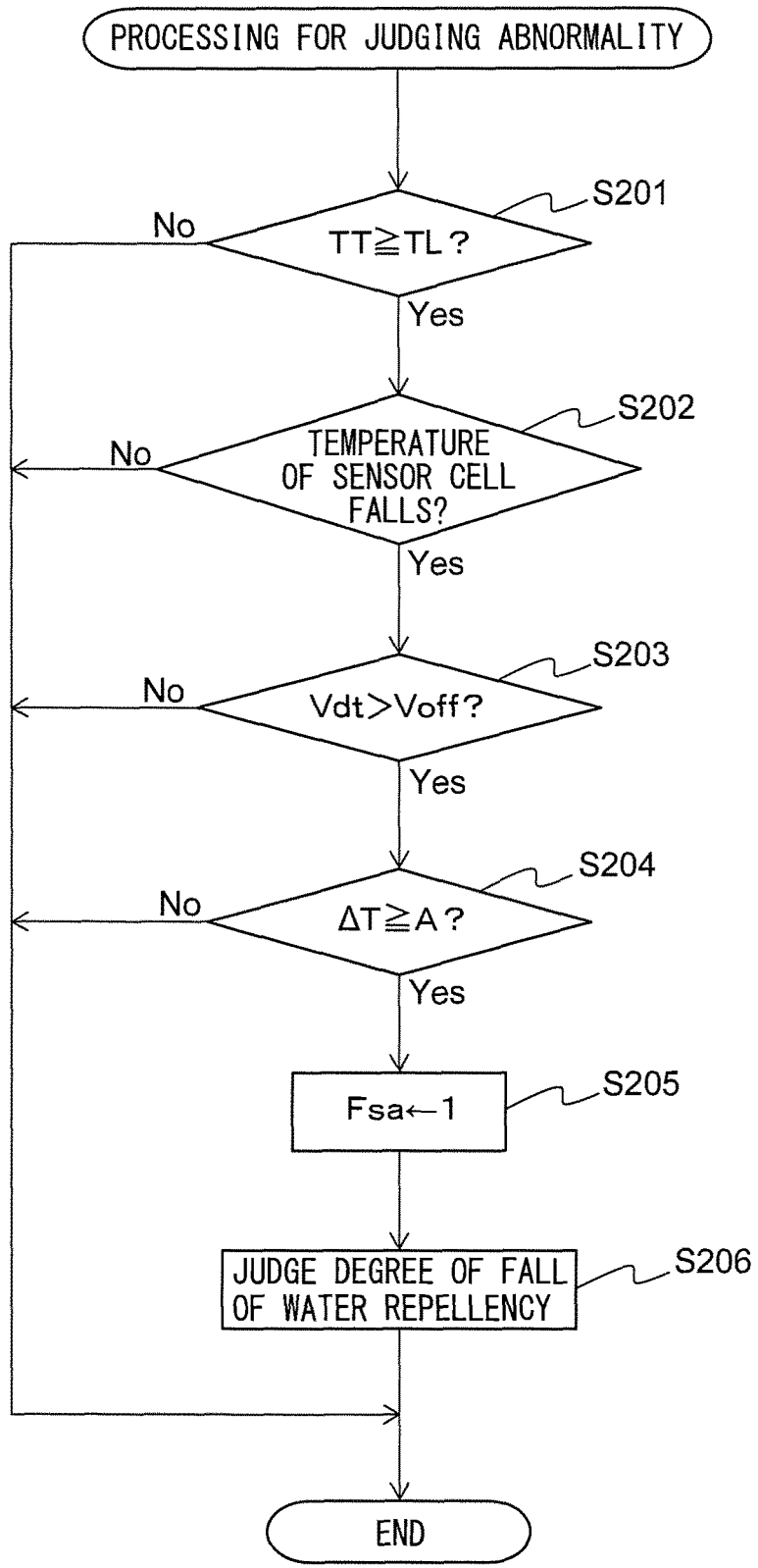
FIG. 8 is a flow chart showing a control routine of processing for judging abnormality in the second embodiment of the present invention.

FIG. 8 is a flow chart showing a control routine of processing for judging abnormality in the second embodiment of the present invention. The present control routine is repeatedly performed by the ECU 80 at predetermined time intervals after the startup of the internal combustion engine 1. Step S201 to step S203 in FIG. 8 are similar to step S101 to step S103 in FIG. 6, so explanations will be omitted.

The present control routine proceeds to step S204 if at step S203 it is judged that the speed of fall Vdt is faster than the speed of fall Voff. At step S204, the judging part 80c judges whether the amount of fall ΔT of the temperature of the sensor cell 51 from the target temperature TT is a predetermined amount A or more. The amount of fall ΔT is detected by the cell temperature detecting part 80a. The predetermined amount A is for example 15° C. If at step S204 it is judged that the amount of fall ΔT is the predetermined amount A or more, the present control routine proceeds to step S205.

At step S205, the judging part 80c judges that the water repellency of the protective layer 60 is falling and sets the sensor abnormality flag Fsa to "1". The initial value of the sensor abnormality flag Fsa is zero. Further, the sensor abnormality flag Fsa is made zero when the ignition switch of the vehicle carrying the internal combustion engine 1 is turned off or when the internal combustion engine 1 is stopped.

Next, at step S206, the judging part 80c judges the degree of fall of the water repellency of the protective layer 60. The judging part 80c judges the degree of fall of the water repellency of the protective layer 60 to be larger the larger the amount of fall of the temperature of the sensor cell 51 from the target temperature when the temperature falls from the target temperature at a speed faster than the speed of fall of the temperature of the sensor cell 51 when turning the heater 55 off. Specifically, the judging part 80c uses a map such as shown in FIG. 7 to calculate the degree of fall of the water repellency of the protective layer 60 based on the amount of fall ΔT of the temperature of the sensor cell 51 from the target temperature TT. After step S206, the present control routine is ended.

On the other hand, if at step S204 the amount of fall ΔT is less than the predetermined amount A, the present control routine is ended.

<Third Embodiment>

The configuration and control of the control device of an exhaust sensor according to a third embodiment are basically similar to the configuration and control of the control device of an exhaust sensor according to the first embodiment except for the points explained below. For this reason, below, the third embodiment of the present invention will be explained centered on the parts different from the first embodiment.

The water penetrating the protective layer 60 evaporates in the protective layer 60. For this reason, if the protective layer 60 is covered by water when the water repellency of the protective layer 60 is falling, the temperature of the sensor cell 51 will fall from the target temperature, then will again rise to the target temperature. Further, the time period from when the temperature of the sensor cell 51 falls from the target temperature to when it rises to the target temperature is shorter than the ignition period of the internal combustion engine 1 (time interval from when ignition is performed in a certain cylinder to when ignition is performed in the next cylinder). For this reason, in the third embodiment, the condition for judging abnormality includes the temperature of the sensor cell 51 falling from the target temperature then rising to the target temperature and the time period from when the temperature of the sensor cell 51 falls from the target temperature to when it rises to the target temperature being shorter than the ignition period of the internal combustion engine 1. The time period from when the temperature of the sensor cell 51 falls from the target temperature to when it rises to the target temperature is detected by the cell temperature detecting part 80a. The ignition period in the internal combustion engine 1 is calculated based on the number of cylinders of the internal combustion engine 1 and the engine speed. The engine speed is detected by the crank angle sensor 108.

Figure 9:
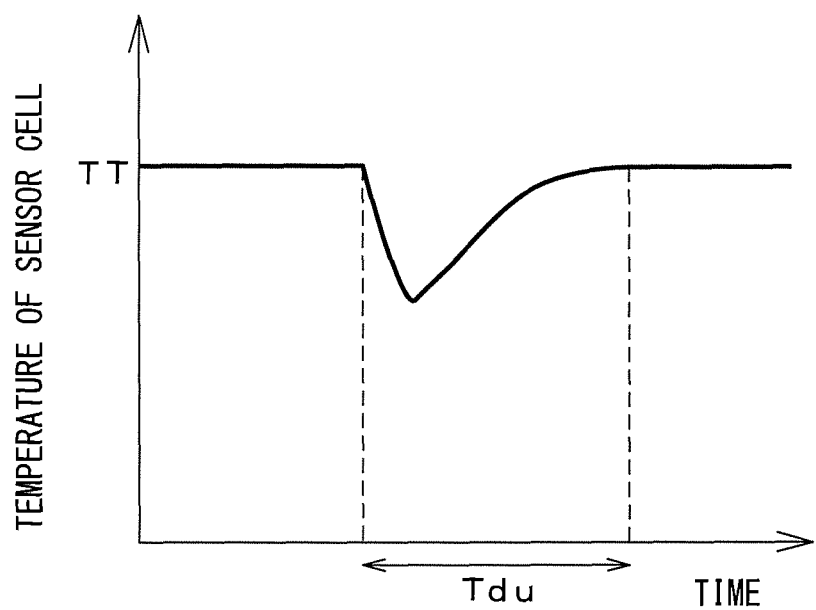
FIG. 9 is a schematic time chart of the temperature of a sensor cell detected by a cell temperature detecting part when the water repellency of the protective layer falls.

FIG. 9 is a schematic time chart of the temperature of the sensor cell 51 detected by the cell temperature detecting part 80a when the water repellency of the protective layer 60 is falling. FIG. 9 shows the time period Tdu from when the temperature of the sensor cell 51 falls from the target temperature TT to when it rises to the target temperature TT.

Further, when coverage by water causes the temperature of the sensor cell 51 to change, the speed of fall and speed of rise of the temperature of the sensor cell 51 become a predetermined speed or more. For this reason, in the third embodiment, the condition for judging abnormality includes the temperature of the sensor cell 51 falling from the target temperature, then rising to the target temperature and the speed of fall and speed of rise of the temperature of the sensor cell 51 being a predetermined speed or more. The speed of fall and speed of rise of the temperature are detected by the cell temperature detecting part 80a. Further, the predetermined speed is determined in advance by experiments or calculations and is, for example, 1500 (° C./sec).

Further, if water penetrates the protective layer 60, since time is taken for the water to evaporate, the speed of rise of the temperature of the sensor cell 51 becomes slower than the speed of fall of the temperature of the sensor cell 51. For this reason, in the third embodiment, the condition for judging abnormality includes the temperature of the sensor cell 51 falling from the target temperature, then rising to the target temperature and the speed of fall of the temperature of the sensor cell 51 being faster than the speed of rise of the temperature of the sensor cell 51.

In the third embodiment, it is possible to suppress misjudging that the water repellency of the protective layer 60 is falling by detecting a change in the temperature of the sensor cell 51 due to factors other than coverage by water, so it is possible to more precisely detect the water repellency of the protective layer 60.

<Control Routine of Processing for Judging Abnormality>

Figure 10:
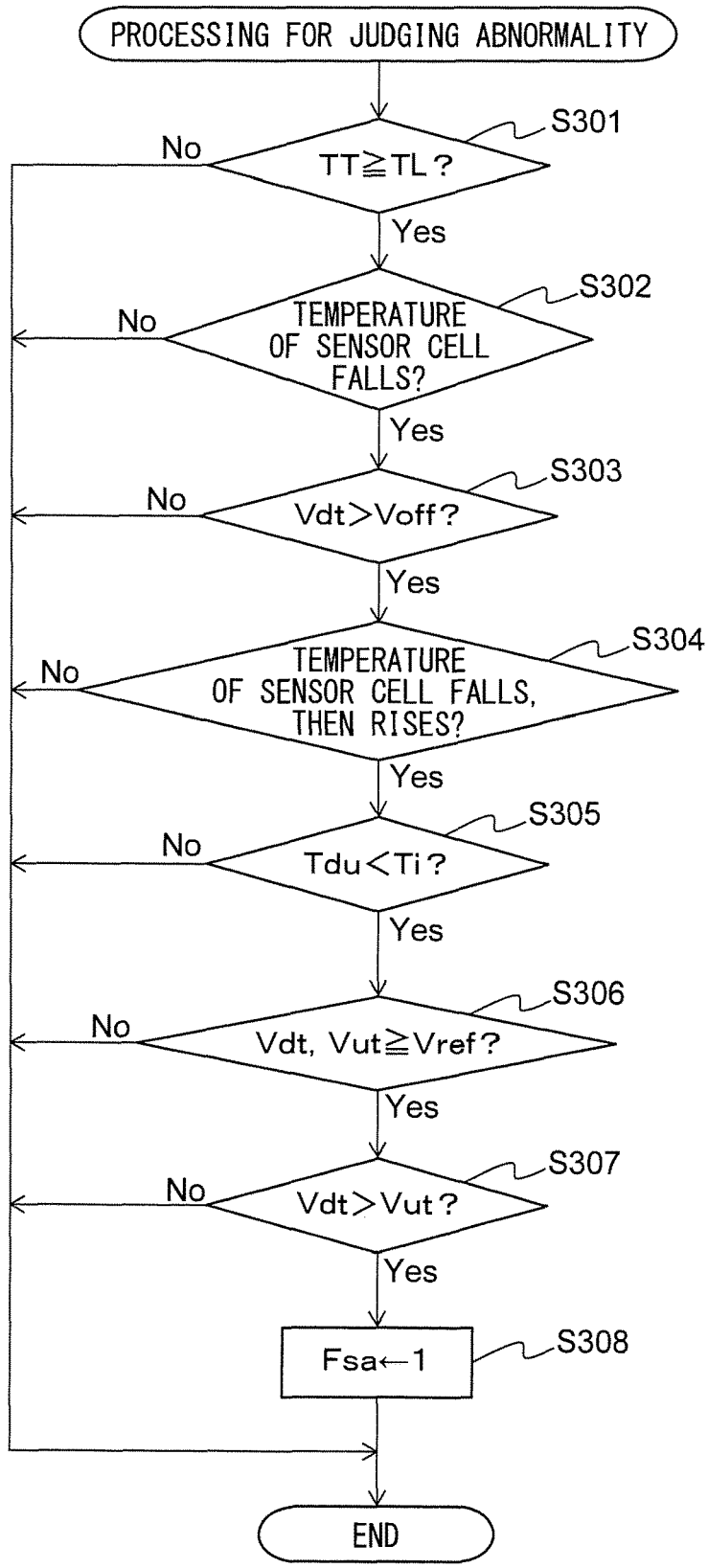
FIG. 10 is a flow chart showing a control routine of processing for judging abnormality in the third embodiment of the present invention.

FIG. 10 is a flow chart showing a control routine of processing for judging abnormality in a third embodiment of the present invention. The present control routine is repeatedly performed by the ECU 80 at predetermined time intervals after the startup of the internal combustion engine 1. Step S301 to step S303 in FIG. 10 are similar to step S101 to step S103 in FIG. 6, so explanations will be omitted.

The present control routine proceeds to step S304 if at step S303 it is judged that the speed of fall Vdt is faster than the speed of fall Voff. At step S304, the judging part 80c judges whether the temperature of the sensor cell 51 fell from the target temperature TT, then rose to the target temperature TT. If at step S304 it is judged that the temperature of the sensor cell 51 fell from the target temperature TT, then rose to the target temperature TT, the present control routine proceeds to step S305.

At step S305, the judging part 80c judges whether the time period Tdu from when the temperature of the sensor cell 51 falls from the target temperature TT to when it rises to the target temperature TT is shorter than the ignition period Ti in the internal combustion engine 1. The time period Tdu is detected by the cell temperature detecting part 80a. The ignition period Ti in the internal combustion engine 1 is calculated based on the number of cylinders of the internal combustion engine 1 and the engine speed. If at step S305 it is judged that the time period Tdu is shorter than the ignition period Ti, the present control routine proceeds to step S306.

At step S306, the judging part 80c judges whether the speed of fall Vdt and the speed of rise Vut of the temperature of the sensor cell 51 Vdt are a predetermined speed Vref or more. The speed of fall Vdt and the speed of rise Vut of the temperature of the sensor cell 51 are detected by the cell temperature detecting part 80a. The predetermined speed Vref is for example 1500 (° C./sec). If at step S306 it is judged that the speed of fall Vdt and the speed of rise Vut are the predetermined speed Vref or more, the present control routine proceeds to step S307.

At step S307, the judging part 80c judges whether the speed of fall Vdt of the temperature of the sensor cell 51 is faster than the speed of rise Vut of the temperature of the sensor cell 51. If at step S307 it is judged that the speed of fall Vdt is faster than the speed of rise Vut of the temperature, the present control routine proceeds to step S308.

At step S308, the judging part 80c judges that the water repellency of the protective layer 60 is falling and sets the sensor abnormality flag Fsa to "1". The initial value of the sensor abnormality flag Fsa is zero. Further, the sensor abnormality flag Fsa is made zero when the ignition switch of the vehicle carrying the internal combustion engine 1 is turned off or when the internal combustion engine 1 is stopped. After step S308, the present control routine is ended.

On the other hand, if at step S304 it is judged that the temperature of the sensor cell 51 did not fall from the target temperature TT, then rise to the target temperature TT, if at step S305 it is judged that the time period Tdu is the ignition period Ti or more, if at step S306 it is judged that the speed of fall Vdt and the speed of rise Vut are less than the predetermined speed Vref, or if at step S307 it is judged that the speed of fall Vdt is the speed of rise Vut of the temperature or less, the present control routine is ended.

Note that, in the present control routine, any one or two of step S305 to step S307 may be omitted.

<Fourth Embodiment>

The configuration and control of the control device of an exhaust sensor according to a fourth embodiment are basically similar to the configuration and control of the control device of an exhaust sensor according to the first embodiment except for the points explained below. For this reason, below, the fourth embodiment of the present invention will be explained centered on the parts different from the first embodiment.

Figure 11:
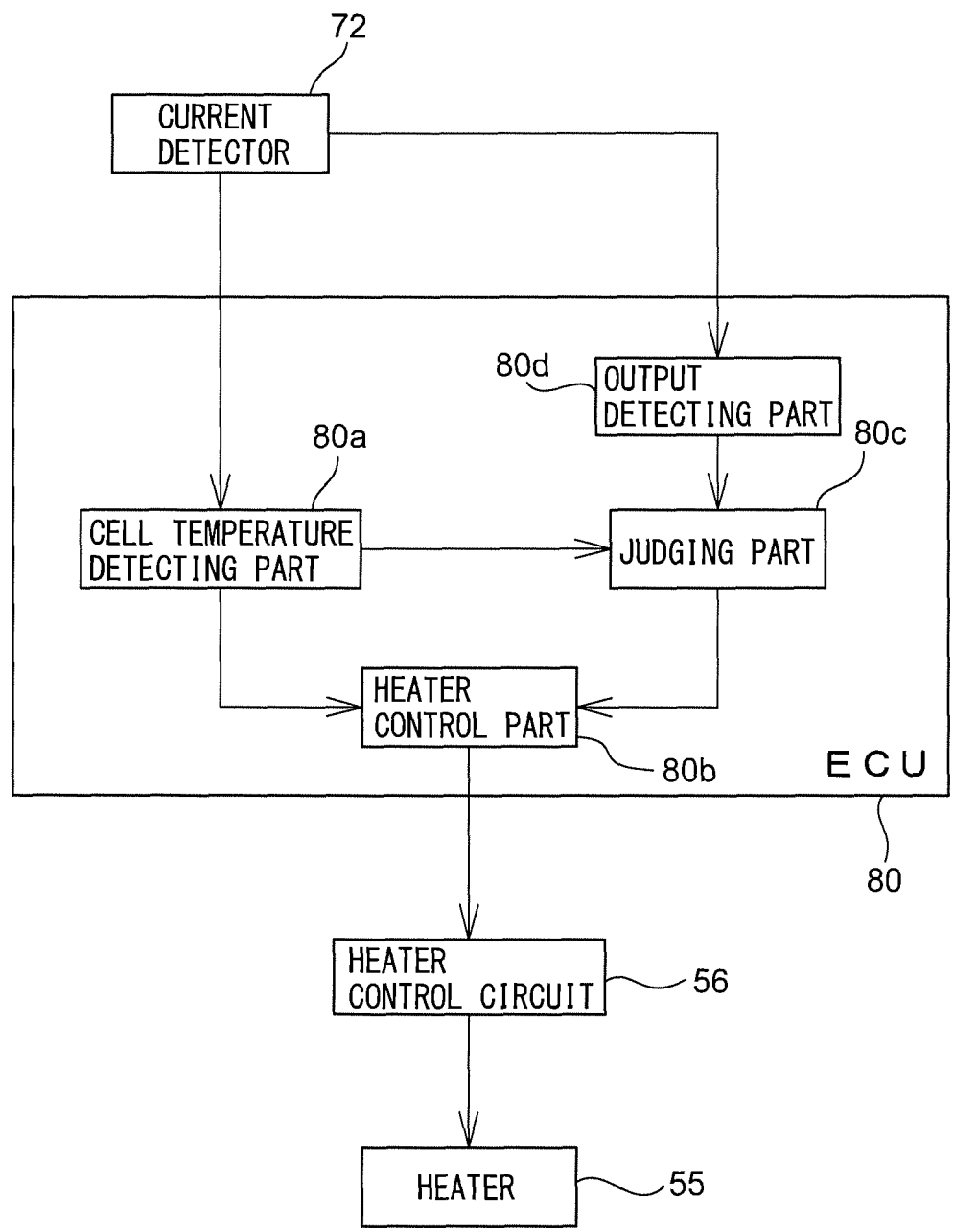
FIG. 11 is a block diagram schematically showing the configuration of a control device of an exhaust sensor etc. according to the fourth embodiment of the present invention.

FIG. 11 is a block diagram schematically showing the configuration of a control device of an exhaust sensor according to the fourth embodiment of the present invention. The control device of an exhaust sensor is further provided with an output detecting part 80d. The output detecting part 80d detects the output of the air-fuel ratio sensor 10 detected by the current detector 72. In the present embodiment, the output detecting part 80d is part of the ECU 80.

If the water repellency of the protective layer 60 falls, part of the water striking the protective layer 60 penetrates the protective layer 60. As a result, exhaust gas is obstructed from passing through the diffusion regulating layer 16 and flowing into the measured gas chamber 30. For this reason, if the protective layer 60 is covered by water when the absolute value of the output of the air-fuel ratio sensor 10 is the value of a reference value or more and the water repellency of the protective layer 60 is falling, the absolute value of the output of the air-fuel ratio sensor 10 will fall toward zero.

For this reason, in the fourth embodiment, the condition for judging abnormality includes the absolute value of the output of the air-fuel ratio sensor 10 detected by the output detecting part 80d falling from a value of the reference value or more when the temperature of the sensor cell 51 falls from the target temperature. The reference value is determined in advance and is, for example, the value of the output corresponding to an air-fuel ratio of 14.65 or the absolute value of the output corresponding to an air-fuel ratio of 14.55.

Further, if the protective layer 60 is covered by water and the absolute value of the output of the air-fuel ratio sensor 10 falls from a value of the reference value or more when the water repellency of the protective layer 60 is falling—the amount of fall from a value of a reference value of the absolute value of the output of the air-fuel ratio sensor 10 or from more becomes a predetermined amount or more. For this reason, in the fourth embodiment, the condition for judging abnormality includes the amount of fall from a reference value of an absolute value of the output of the air-fuel ratio sensor 10 or more being a predetermined amount or more. The predetermined amount is determined in advance by experiments or calculations and for example is 10% of the absolute value of the output before the fall.

Further, if the protective layer 60 is covered by water when the water repellency of the protective layer 60 falls, the absolute value of the output of the air-fuel ratio sensor 10 falls from a value of the reference value or more, then again rises to a value of the reference value or more. Further, the time period from when the absolute value of the output of the air-fuel ratio sensor 10 falls from a value of a reference value or more to when it rises to a value of the reference value or more is shorter than the ignition period in the internal combustion engine 1. For this reason, in the fourth embodiment, the condition for judging abnormality includes the absolute value of the output of the air-fuel ratio sensor 10 falling from a value of the reference value or more, then rising to a value of the reference value or more and the time period from when the absolute value of the output of the air-fuel ratio sensor 10 falls from a value of the reference value or more to when it rises to a value of the reference value or more being shorter than the ignition period in the internal combustion engine 1. The time period from when the absolute value of the output of the air-fuel ratio sensor 10 falls from a value of the reference value or more to when it rises to a value of the reference value or more is detected by the output detecting part 80d. The ignition period at the internal combustion engine 1 is calculated based on the number of cylinders of the internal combustion engine 1 and the engine speed. The engine speed is detected by the crank angle sensor 108.

Further, if the absolute value of the output of the air-fuel ratio sensor 10 changes due to coverage by water, the speed of fall and the speed of rise of the absolute value of the output of the air-fuel ratio sensor 10 becomes a predetermined speed or more. For this reason, in the fourth embodiment, the condition for judging abnormality includes the absolute value of the output of the air-fuel ratio sensor 10 falling from a value of a reference value or more, then rising to a value of the reference value or more and the speed of fall and the speed of rise of the absolute value of the output being a predetermined speed or more. The speed of fall and the speed of rise of the absolute value of the output are detected by the output detecting part 80d. Further, the predetermined speed is determined in advance by experiments or calculations and, for example, is the rate of change of output corresponding to a rate of change of air-fuel ratio of 100/sec. Note that, this value is larger than the amount of change of output occurring due to normal combustion.

Further, if water penetrates the protective layer 60, since time is taken for the water to evaporate, the speed of rise of the absolute value of the output of the air-fuel ratio sensor 10 becomes slower than the speed of fall of the absolute value of the output. For this reason, in the fourth embodiment, the condition for judging abnormality includes the absolute value of the output of the air-fuel ratio sensor 10 falling from a value of the reference value or more, then rising to a value of the reference value or more and the speed of fall of the absolute value of the output being faster than the speed of rise of the absolute value of the output.

Further, when the air-fuel ratio of the exhaust gas introduced into the measured gas chamber 30 is at the stoichiometric air-fuel ratio (14.60), the output of the air-fuel ratio sensor 10 becomes substantially zero. However, if the water repellency of the protective layer 60 falls, the concentration of water in the exhaust gas introduced into the measured gas chamber 30 becomes higher and part of the oxygen atoms in the water molecules are broken down at the sensor cell 51. As a result, if the protective layer 60 is covered by water when the output of the air-fuel ratio sensor 10 is a value in a near zero region and the water repellency of the protective layer 60 is falling, the output of the air-fuel ratio sensor 10 temporarily rises.

For this reason, in the fourth embodiment, the condition for judging abnormality includes the output of the air-fuel ratio sensor 10 detected by the output detecting part 80*d* rising from a value in the near zero region when the temperature of the sensor cell 51 falls. The near zero region is determined in advance and is a range of output corresponding to a range of air-fuel ratio of, for example, 14.55 to 14.65.

Further, the time period from when the output of the air-fuel ratio sensor 10 rises from a value in the near zero region to when it falls to a value in the near zero region is shorter than the ignition period of the internal combustion engine 1. For this reason, in the fourth embodiment, the condition for judging abnormality includes the output of the air-fuel ratio sensor 10 rising from a value in the near zero region, then falling to a value in the near zero region and the time period from when the output of the air-fuel ratio sensor 10 rises from a value in the near zero region to when it falls to a value in the near zero region being shorter than the ignition period in the internal combustion engine 1. The time period from when the output of the air-fuel ratio sensor 10 rises from a value in the near zero region, then falls to a value in the near zero region is detected by the output detecting part 80*d*. The ignition period in the internal combustion engine 1 is calculated based on the number of cylinders of the internal combustion engine 1 and the engine speed. The engine speed is detected by the crank angle sensor 108.

In the fourth embodiment, it is possible to suppress misjudging that the water repellency of the protective layer 60 is falling by judging a fall in the water repellency of the protective layer 60 based on not only the change of the temperature of the sensor cell 51 but also the change of the output of the air-fuel ratio sensor 10, so it is possible to more precisely detect a fall in the water repellency of the protective layer 60.

<Control Routine of Processing for Judging Abnormality>

Figure 12:
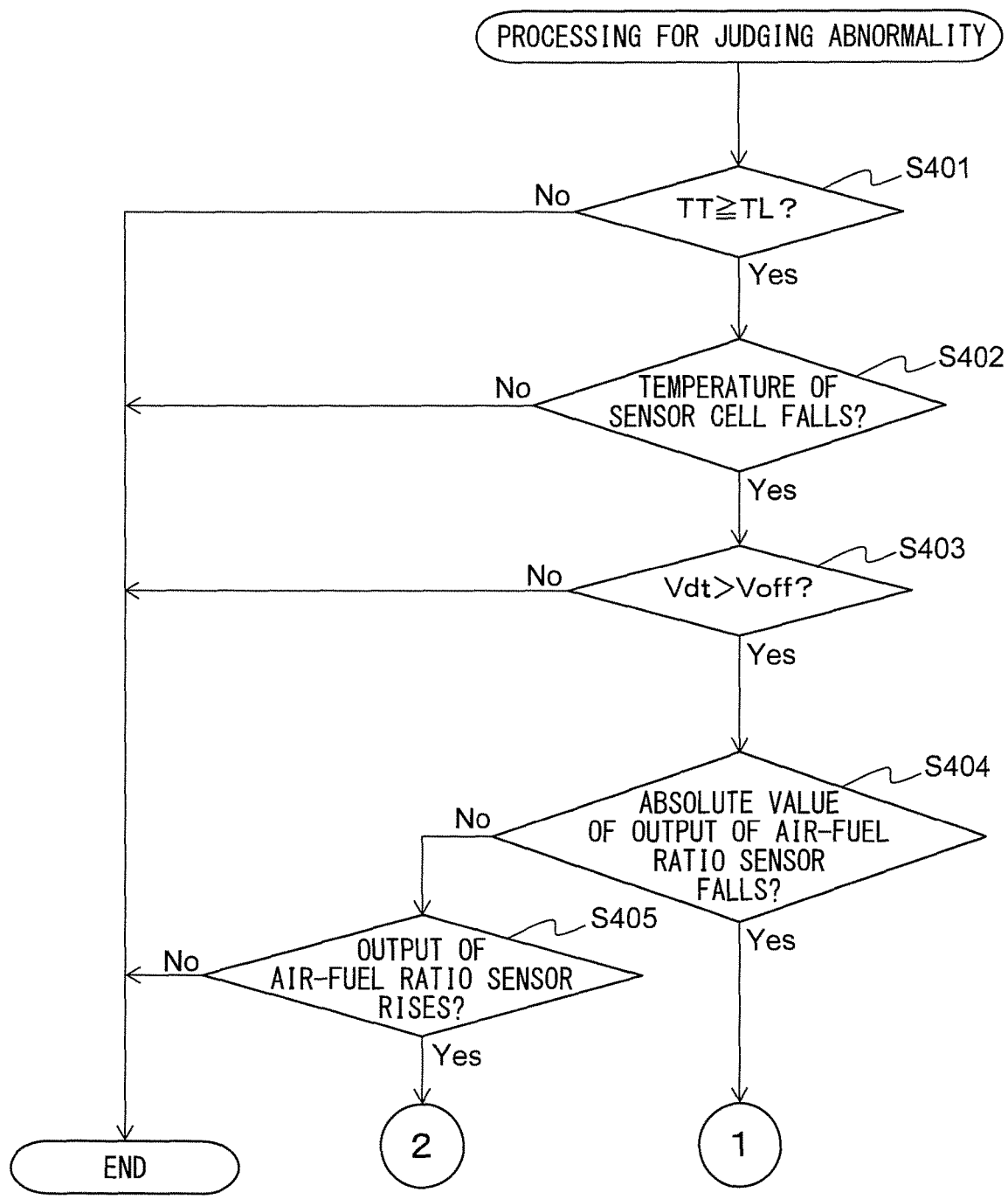
FIG. 12 is a flow chart showing a control routine of processing for judging abnormality in the fourth embodiment of the present invention.
Figure 13:
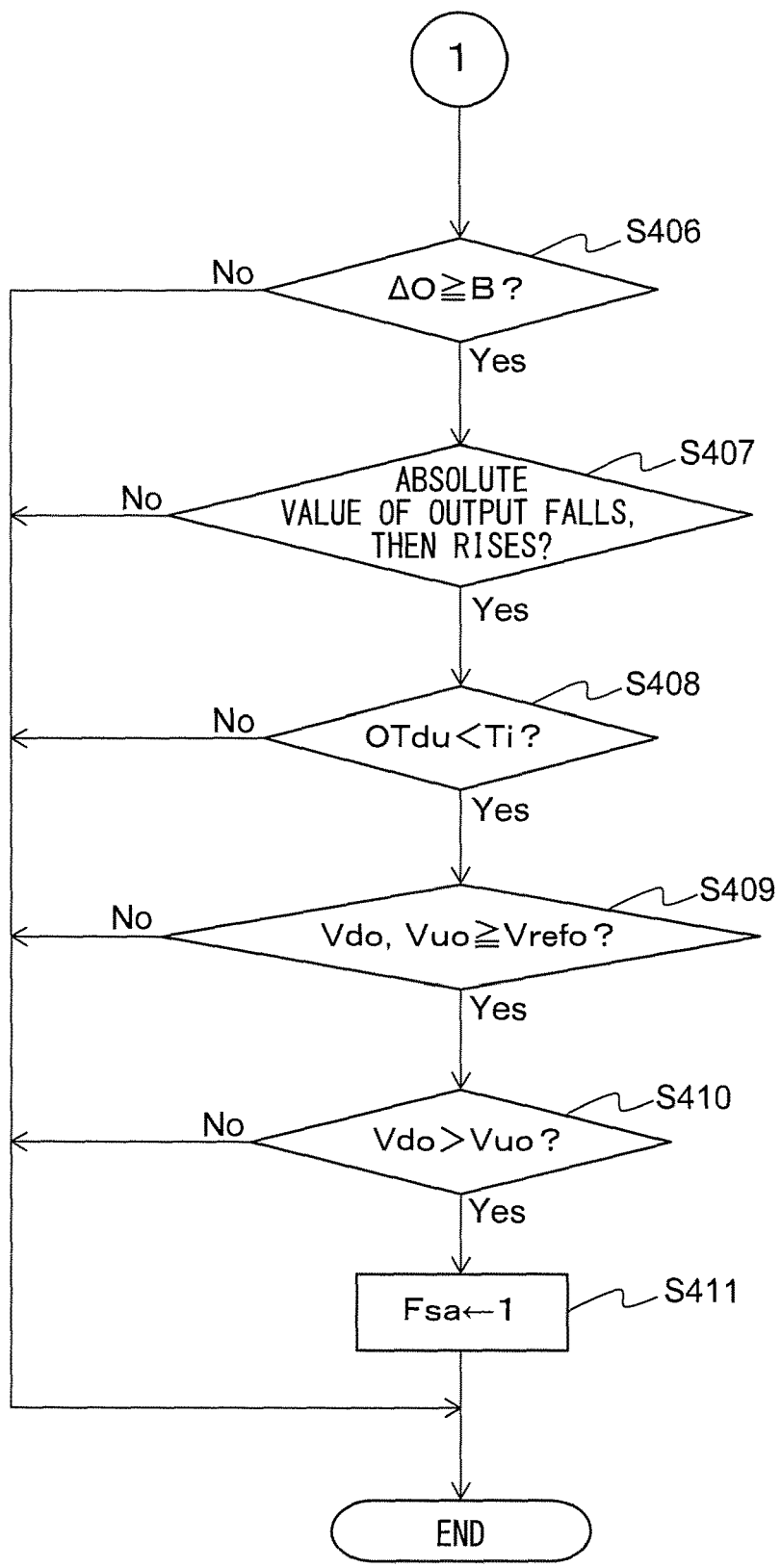
FIG. 13 is a flow chart showing a control routine of processing for judging abnormality in the fourth embodiment of the present invention.
Figure 14:
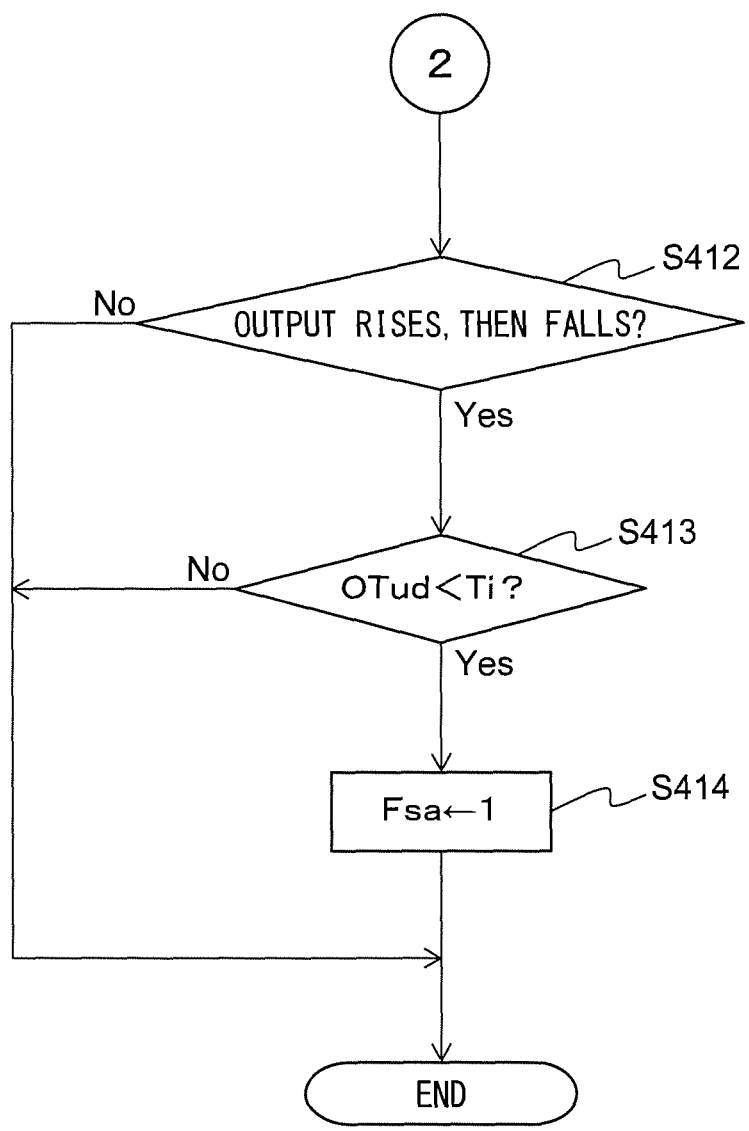
FIG. 14 is a flow chart showing a control routine of processing for judging abnormality in the fourth embodiment of the present invention.

FIG. 12 to FIG. 14 are flow charts showing a control routine of processing for judging abnormality in a fourth embodiment of the present invention. The present control routine is repeatedly performed by the ECU 80 at predetermined time intervals after the startup of the internal combustion engine 1. Step S401 to step S403 in FIG. 12 are similar to step S101 to step S103 in FIG. 6, so explanations will be omitted.

The present control routine proceeds to step S404 if at step S403 it is judged that the speed of fall Vdt is faster than the speed of fall Voff. At step S404, the judging part 80*c* judges whether the absolute value of the output of the air-fuel ratio sensor 10 is falling from a value of the reference value or more. The absolute value of the output of the air-fuel ratio sensor 10 is detected by the output detecting part 80*d*. The reference value is, for example, the value of the output corresponding to an air-fuel ratio of 14.65 or the absolute value of the output corresponding to an air-fuel ratio of 14.55. If at step S404 it is judged that the absolute value of the output of the air-fuel ratio sensor 10 is falling from a value of the reference value or more, the present control routine proceeds to step S406.

At step S406, the judging part 80*c* judges whether the amount of fall ΔO from a value of the reference value of the absolute value of the output of the air-fuel ratio sensor 10 or more is a predetermined amount B or more. The predetermined amount B is, for example, 10% of the absolute value of the output before the fall. If at step S406 it is judged that the amount of fall ΔO is the predetermined amount B or more, the present control routine proceeds to step S407.

At step S407, the judging part 80*c* judges whether the absolute value of the output of the air-fuel ratio sensor 10 fell from a value of the reference value or more, then rose to a value of the reference value or more. If at step S407 it is judged that the absolute value of the output of the air-fuel ratio sensor 10 fell from a value of the reference value or more, then rose to a value of the reference value or more, the present control routine proceeds to step S408.

At step S408, it is judged whether the time period OTdu from when the absolute value of the output of the air-fuel ratio sensor 10 fell from a value of the reference value or more, then rose to a value of the reference value or more is shorter than the ignition period Ti in the internal combustion engine 1. The time period OTdu is detected by the output detecting part 80*d*. The ignition period Ti in the internal combustion engine 1 is calculated based on the number of cylinders of the internal combustion engine 1 and the engine speed. If at step S408 it is judged that the time period OTdu is shorter than the ignition period Ti, the present control routine proceeds to step S409.

At step S409, the judging part 80*c* judges whether the speed of fall Vdo and the speed of rise Vuo of the absolute value of the output of the air-fuel ratio sensor 10 are a predetermined speed Vrefo or more. The speed of fall Vdo and the speed of rise Vuo are detected by the output detecting part 80*d*. The predetermined speed Vrefo, for example, is the rate of change of output corresponding to a rate of change of air-fuel ratio of 100/sec. If at step S409 it is judged that the speed of fall Vdo and the speed of rise Vuo are the predetermined speed Vrefo or more, the present control routine proceeds to step S410.

At step S410, the judging part 80*c* judges whether the speed of fall Vdo is faster than the speed of rise Vuo. If at step S410 it is judged that the speed of fall Vdo is faster than the speed of rise Vuo, the present control routine proceeds to step S411.

At step S411, the judging part 80*c* judges that the water repellency of the protective layer 60 is falling and sets the sensor abnormality flag Fsa to "1". The initial value of the sensor abnormality flag Fsa is zero. Further, the sensor abnormality flag Fsa is made zero when the ignition switch of the vehicle carrying the internal combustion engine 1 is turned off or when the internal combustion engine 1 is stopped. After step S411, the present control routine is ended.

On the other hand, if at step S406 it is judged that the amount of fall ΔO is less than a predetermined amount B, if at step S407 it is judged that the absolute value of the output of the air-fuel ratio sensor 10 did not fall from a value of the reference value or more, then rise to a value of the reference value or more, if at step S408 it is judged that the time period OTdu is the ignition period Ti or more, if at step S409 it is judged that speed of fall Vdo and the speed of rise Vuo are less than a predetermined speed Vrefo, or if at step S410 it is judged that the speed of fall Vdo is the speed of rise Vuo or less, the present control routine is ended.

Further, if at step S404 it is judged that the absolute value of the output of the air-fuel ratio sensor 10 has not fallen from a value of the reference value or more, the present control routine proceeds to step S405. At step S405, the judging part 80c judges whether the output of the air-fuel ratio sensor 10 has risen from a value in the near zero region. The near zero region is for example a range of output corresponding to a range of air-fuel ratio of 14.55 to 14.65. If at step S405 it is judged that the output of the air-fuel ratio sensor 10 has risen from a value in the near zero region, the present control routine proceeds to step S412.

At step S412, the judging part 80c judges whether the output of the air-fuel ratio sensor 10 rose from a value in the near zero region, then fell to a value in the near zero region. If at step S412 it is judged that the output of the air-fuel ratio sensor 10 rose from a value in the near zero region, then fell to a value in the near zero region, the present control routine proceeds to step S413.

At step S413, it is judged whether the time period OTud from when the output of the air-fuel ratio sensor 10 rose from a value in the near zero region to when it fell to a value in the near zero region is shorter than the ignition period Ti in the internal combustion engine 1. The time period OTud is detected by the output detecting part 80d. The ignition period Ti in the internal combustion engine 1 is calculated based on the number of cylinders of the internal combustion engine 1 and the engine speed. If at step S413 it is judged that the time period OTud is shorter than the ignition period Ti, the present control routine proceeds to step S414.

At step S414, the judging part 80c judges that the water repellency of the protective layer 60 is falling and sets the sensor abnormality flag Fsa to "1". After step S414, the present control routine is ended.

On the other hand, if at step S405 it is judged that the output of the air-fuel ratio sensor 10 did not rise from a value in the near zero region, if at step S412 it is judged that the output of the air-fuel ratio sensor 10 did not rise from a value in the near zero region, then fall to a value in the near zero region, or if at step S413 it is judged that the time period OTud is the ignition period Ti or more, the present control routine is ended.

Note that, in the present control routine, step S404 and step S406 to step S411 may be omitted. In this case, if at step S403 it is judged that the speed of fall Vdt is faster than the speed of fall Voff, the present control routine proceeds to step S405. Further, in the present control routine, step S405 and step S412 to step S414 may be omitted. In this case, if at step S404 it is judged that the absolute value of the output of the air-fuel ratio sensor 10 has not fallen from a value of the reference value or more, the present control routine is ended. Further, any six or fewer steps in step S406 to step S410 and step S412 to step S413 may be omitted.

<Fifth Embodiment>

The configuration and control of the control device of an exhaust sensor according to a fifth embodiment are basically similar to the configuration and control of the control device of an exhaust sensor according to the first embodiment except for the points explained below. For this reason, below, the fifth embodiment of the present invention will be explained centered on the parts different from the first embodiment.

Figure 15:
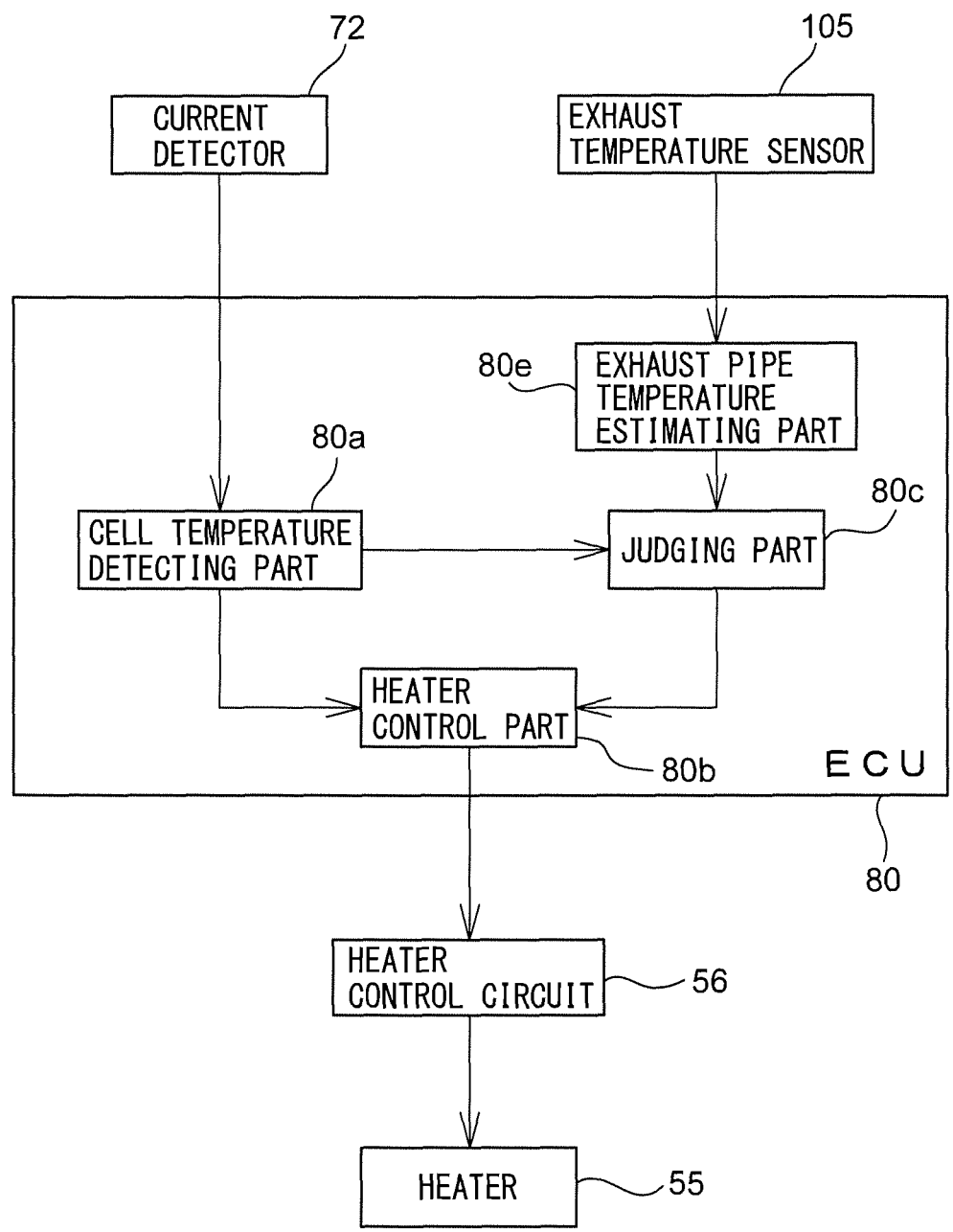
FIG. 15 is a block diagram schematically showing the configuration of a control device of an exhaust sensor etc. according to the fifth embodiment of the present invention.

FIG. 15 is a block diagram schematically showing the configuration of a control device of an exhaust sensor according to the fifth embodiment of the present invention. The control device of an exhaust sensor is further provided with an exhaust pipe temperature estimating part 80e. In the present embodiment, the exhaust pipe temperature estimating part 80e is part of the ECU 80.

Figure 16:
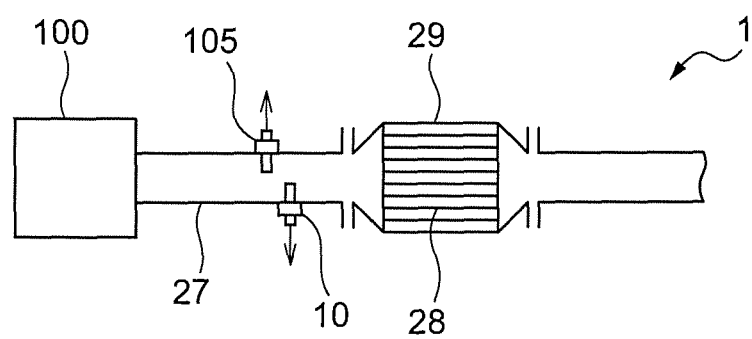
FIG. 16 is a view schematically showing an internal combustion engine in which a control device of an exhaust sensor according to the fifth embodiment of the present invention is used.

The exhaust pipe temperature estimating part 80e estimates the temperature of the exhaust pipe 27 around the air-fuel ratio sensor 10 (below, simply referred to as the "temperature of the exhaust pipe 27"). FIG. 16 is a view schematically showing an internal combustion engine 1 in which a control device of an exhaust sensor according to the fifth embodiment of the present invention is used. For example, the exhaust pipe temperature estimating part 80e estimates the temperature of the exhaust pipe 27 from the output of the exhaust temperature sensor 105 arranged in the exhaust passage near the air-fuel ratio sensor 10. The exhaust temperature sensor 105 is arranged near the air-fuel ratio sensor 10 and detects the temperature of the exhaust pipe 27. The output of the exhaust temperature sensor 105 is input through the corresponding AD converter 87 to the input port 85 of the ECU 80.

Note that, the exhaust pipe temperature estimating part 80e may estimate the temperature of the exhaust pipe 27 without using the exhaust temperature sensor 105. In this case, the internal combustion engine 1 need not be provided with the exhaust temperature sensor 105 near the air-fuel ratio sensor 10. For example, the exhaust pipe temperature estimating part 80e may estimate the temperature of the exhaust pipe 27 based on the elapsed time from when the internal combustion engine 1 is started up. In this case, the longer the elapsed time from when the internal combustion engine 1 is started up, the higher the temperature of the exhaust pipe 27 estimated by the exhaust pipe temperature estimating part 80e.

Figure 17:
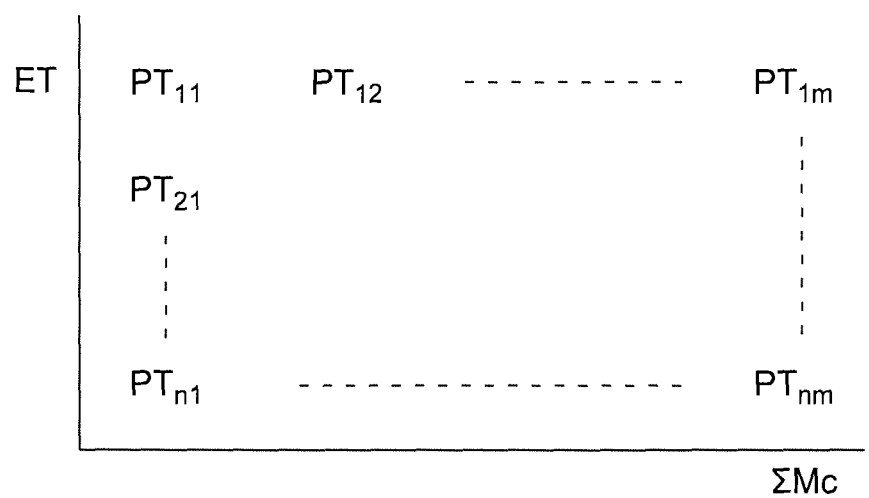
FIG. 17 is a map showing the relationship between an elapsed time and cumulative amount of air, and a temperature of an exhaust pipe.

Further, the exhaust pipe temperature estimating part 80e may estimate the temperature of the exhaust pipe 27 based on the cumulative value of the amount of intake air supplied to a combustion chamber 2 from when the internal combustion engine 1 is started up (below, referred to as "cumulative amount of air"). The cumulative amount of air is, for example, calculated based on the output of the air flow meter 102. In this case, the greater the cumulative amount of air, the higher the temperature of the exhaust pipe 27 estimated by the exhaust pipe temperature estimating part 80e. Further, the exhaust pipe temperature estimating part 80e may estimate the temperature of the exhaust pipe 27 based on the elapsed time and the cumulative amount of air from when the internal combustion engine 1 is started up. In this case, the exhaust pipe temperature estimating part 80e, for example, estimates the temperature of the exhaust pipe 27 using a map such as shown in FIG. 17. In this map, the temperature PT of the exhaust pipe 27 is shown as a function of the elapsed time ET and the cumulative amount of air ΣMc.

Further, the exhaust pipe temperature estimating part 80e may estimate the temperature of the exhaust pipe 27 based on the temperature of the cooling water of the internal combustion engine 1. The temperature of the cooling water is, for example, detected by a water temperature sensor (not shown) arranged in the cooling water path of the internal combustion engine 1.

As explained above, when the temperature of the exhaust pipe 27 is the dew point temperature of water or less, the water vapor in the exhaust gas condenses and condensed water is generated. For this reason, until the temperature of the exhaust pipe 27 reaches the dew point temperature of water, a lot of condensed water strikes the protective layer 60 of the air-fuel ratio sensor 10 together with the exhaust gas. On the other hand, if the temperature of the exhaust pipe 27 reaches the dew point temperature of water, new condensed water will not be generated inside the exhaust passage. For this reason, after the temperature of the exhaust pipe 27 reaches the dew point temperature of water, there is little possibility of the protective layer 60 being covered by water.

Therefore, in the fifth embodiment, after the temperature of the exhaust pipe 27 estimated by the exhaust pipe temperature estimating part 80e reaches a predetermined temperature of the dew point temperature or more, the judging part 80c does not judge whether the water repellency of the protective layer 60 is falling. Due to this, it is possible to suppress misjudging that the water repellency of the protective layer 60 is falling by detecting a change of the temperature of the sensor cell 51 due to factors other than coverage by water, so it is possible to more precisely detect a drop in the water repellency of the protective layer 60.

Further, if the temperature of the exhaust pipe 27 reaches the boiling point of water, the condensed water which remained in the exhaust passage evaporates and condensed water no longer strikes the protective layer 60. For this reason, the above predetermined temperature may be the boiling point of water. Note that, the dew point is 54° C. at atmospheric pressure (1 atm), while the boiling point of water is 100° C. at atmospheric pressure.

<Control Routine of Processing for Judging Abnormality>

Figure 18:
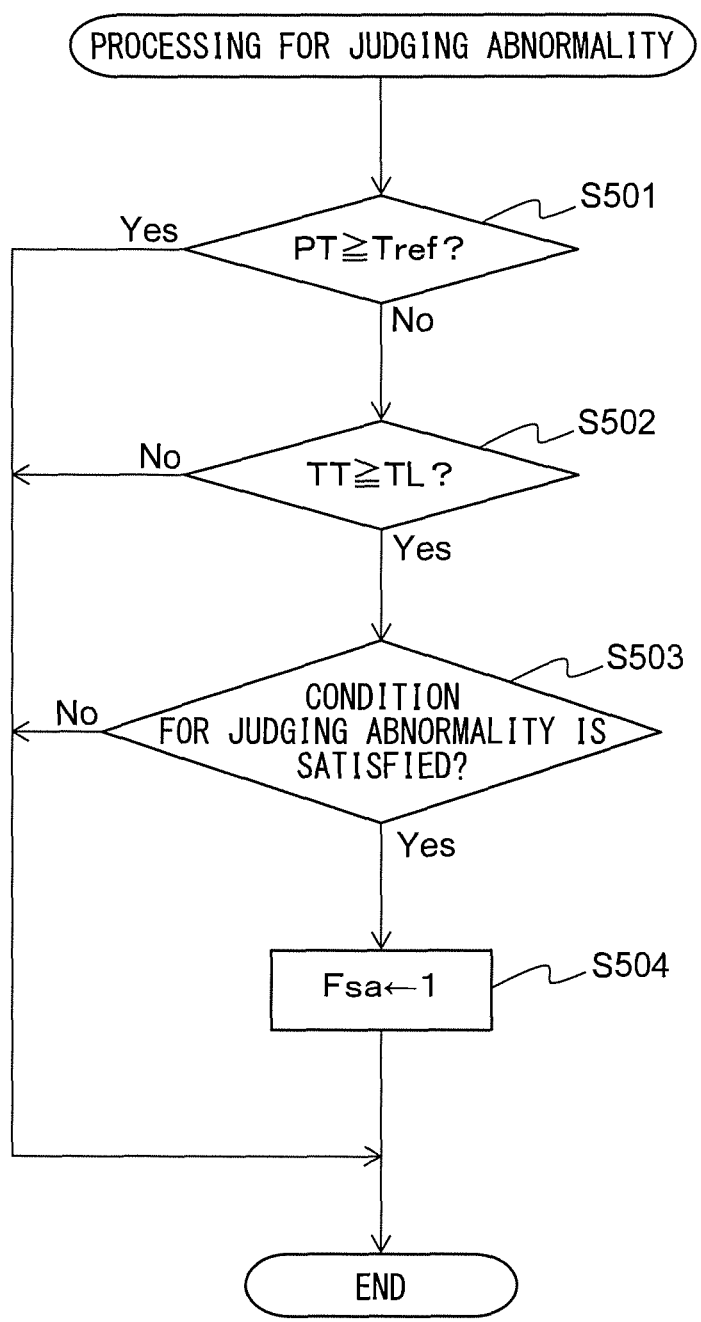
FIG. 18 is a flow chart showing a control routine of processing for judging abnormality in the fifth embodiment of the present invention.

FIG. 18 is a flow chart showing a control routine of processing for judging abnormality in the fifth embodiment of the present invention. The present control routine is repeatedly performed by the ECU 80 at predetermined time intervals after the startup of the internal combustion engine 1.

First, at step S501, the judging part 80c judges whether the temperature PT of the exhaust pipe 27 is a predetermined temperature Tref, which is the dew point temperature or more, or more. The temperature PT of the exhaust pipe 27 is estimated by the exhaust pipe temperature estimating part 80e using any of the above-mentioned methods. The predetermined temperature Tref is for example the dew point or boiling point of water.

If at step S501 it is judged that the temperature PT of the exhaust pipe 27 is a predetermined temperature Tref or more, the present control routine is ended. In this case, it is not judged whether the water repellency of the protective layer 60 is falling. On the other hand, if at step S501 it is judged that the temperature PT of the exhaust pipe 27 is less than a predetermined temperature Tref, the present control routine proceeds to step S502.

At step S502, the judging part 80c judges whether the target temperature TT of the sensor cell 51 set by the heater control part 80b is a temperature of the lowest temperature TL at which the Leidenfrost phenomenon occurs at the outer surface of the protective layer 60 or more. The lowest temperature TL is for example 400° C.

If at step S502 it is judged that the target temperature TT is less than the lowest temperature TL, the present control routine is ended. In this case, it is not judged whether the water repellency of the protective layer 60 is falling. On the other hand, if at step S502 it is judged that the target temperature TT is the lowest temperature TL or more, the present control routine proceeds to step S503.

At step S503, the judging part 80c judges whether the condition for judging abnormality is satisfied. The condition for judging abnormality is at least one of the above-mentioned conditions for judging abnormality in the explanations of the first embodiment to the fourth embodiment.

If at step S503 it is judged that the condition for judging abnormality is satisfied, the present control routine proceeds to step S504. At step S504, the judging part 80c judges that the water repellency of the protective layer 60 is falling and sets the sensor abnormality flag Fsa to "1". The initial value of the sensor abnormality flag Fsa is zero. Further, the sensor abnormality flag Fsa is made zero when the ignition switch of the vehicle carrying the internal combustion engine 1 is turned off or when the internal combustion engine 1 is stopped. After step S504, the present control routine is ended. On the other hand, if at step S503 it is judged that the condition for judging abnormality is not satisfied, the present control routine is ended.

<Sixth Embodiment>

The configuration and control of the control device of an exhaust sensor according to a sixth embodiment are basically similar to the configuration and control of the control device of an exhaust sensor according to the first embodiment except for the points explained below. For this reason, below, the sixth embodiment of the present invention will be explained centered on the parts different from the first embodiment.

As shown in FIG. 4, even if the thermal conductivity of the protective layer 60 falls and the water repellency of the protective layer 60 falls, it is possible to cause the Leidenfrost phenomenon by rising the surface temperature of the protective layer 60. For this reason, in the sixth embodiment, the heater control part 80b rises the target temperature of the sensor cell 51 when the judging part 80c judges that the water repellency of the protective layer 60 is falling. Due to this, even if the water repellency of the protective layer 60 is falling, it is possible to cause the Leidenfrost phenomenon at the outer surface of the protective layer 60 and possible to prevent the element of the air-fuel ratio sensor 10 from cracking.

Further, one of the reasons why the water repellency of the protective layer 60 falls is the deposition of soot on the protective layer 60. For this reason, preferably, the heater control part 80b rises the target temperature of the sensor cell 51 so that the outer surface of the protective layer 60 becomes the combustion temperature of soot or more when the judging part 80c judges that the water repellency of the protective layer 60 is falling. Due to this, it is possible to remove soot from the protective layer 60. Therefore, if deposition of soot on the protective layer 60 causes the water repellency of the protective layer 60 to fall, the water repellency of the protective layer 60 can be restored. The combustion temperature of soot is 750° C. or more. For example, the target temperature of the sensor cell 51 is risen to 750° C. or more.

Further, as will be understood from FIG. 4, the larger the degree of fall of the water repellency of the protective layer 60, the higher the temperature required for causing the Leidenfrost phenomenon becomes. For this reason, if, like in the second embodiment, the judging part 80c judges the degree of fall of the water repellency of the protective layer 60, the heater control part 80b increases the amount of rise of the target temperature of the sensor cell 51 more when the degree of fall of the water repellency of the protective layer 60 is relatively large compared to when the degree of fall of the water repellency of the protective layer 60 is relatively small. Due to this, it is possible to use the Leidenfrost phenomenon to prevent the element of the air-fuel ratio sensor 10 to crack while suppressing an increase in the power consumption of the heater 55 due to rising the target temperature.

Figure 19:
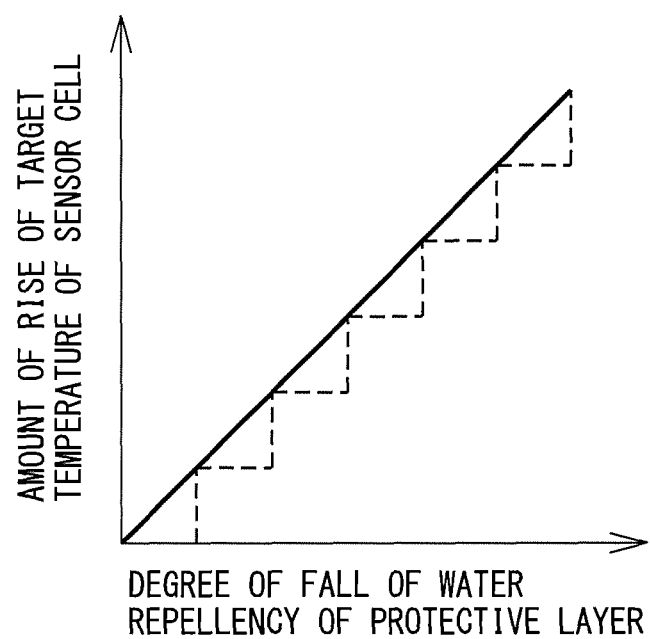
FIG. 19 is a map showing the relationship between an amount of rise of a target temperature of a sensor cell and a degree of fall of water repellency of a protective layer.

The amount of rise of the target temperature of the sensor cell 51 is, for example, calculated using a map such as shown in FIG. 19. In this map, the amount of rise of the target temperature of the sensor cell 51 is shown as a function of the degree of fall of the water repellency of the protective layer 60. Note that, the amount of rise of the target temperature may be made larger in stages (in steps) as the degree of fall of the water repellency becomes larger, as shown in FIG. 19 by the broken line.

<Explanation of Control Using Time Chart>

Figure 20:
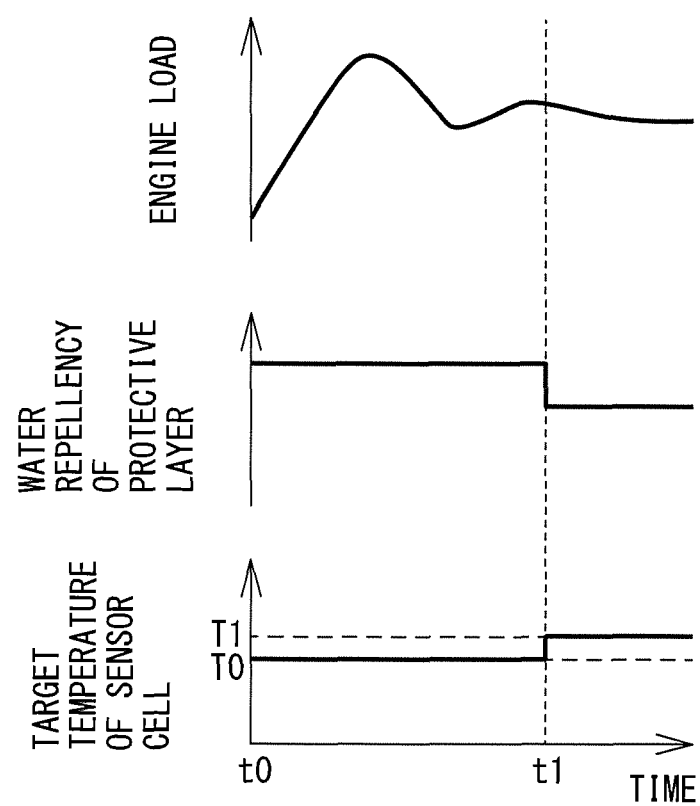
FIG. 20 is a schematic time chart of an engine load, water repellency of the protective layer, and target temperature of a sensor cell after making the internal combustion engine start up.

Below, referring to the time chart of FIG. 20, control performed by the control device of an exhaust sensor in the sixth embodiment will be specifically explained. FIG. 20 is a schematic time chart of the engine load, the water repellency of the protective layer, and target temperature of the sensor cell 51 after starting up the internal combustion engine 1.

In the illustrated example, at the time t0, the internal combustion engine 1 is started up. If the internal combustion engine 1 is started up, the target temperature of the sensor cell 51 is set to the initial temperature T0. The initial temperature T0 is a temperature of the lowest temperature where the Leidenfrost phenomenon occurs at the outer surface of the protective layer 60 or more and is, for example, 750° C.

In the illustrated example, at the time t1, it is judged that the water repellency of the protective layer 60 is falling. For this reason, at the time t1, the target temperature of the sensor cell 51 is risen from the initial temperature T0 to the first temperature T1. The first temperature T1 is a temperature by which the outer surface of the protective layer 60 will become the combustion temperature of soot or more and is for example 800° C.

<Processing for Setting Target Temperature>

Figure 21:
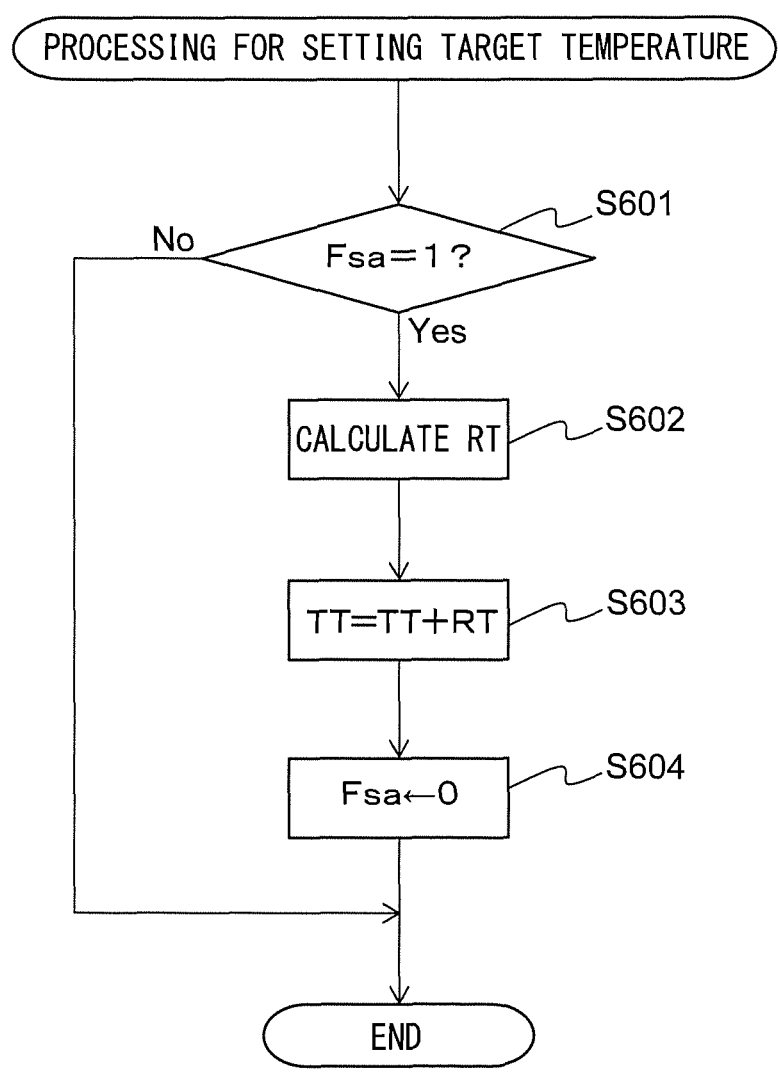
FIG. 21 is a flow chart showing a control routine of processing for setting a target temperature in the sixth embodiment of the present invention.

Below, referring to the flow chart of FIG. 21, control for setting the target temperature of the sensor cell 51 will be explained. FIG. 21 is a flow chart showing the control routine of processing for setting a target temperature in the sixth embodiment of the present invention. The present control routine is repeatedly performed by the ECU 80 at predetermined time intervals after the startup of the internal combustion engine 1.

First, at step S601, the heater control part 80b judges whether the sensor abnormality flag Fsa has been set to "1". If it is judged that the sensor abnormality flag Fsa has been set to "1", the present control routine proceeds to step S602. In this case, the judging part 80c judges that the water repellency of the protective layer 60 is falling.

At step S602, the heater control part 80b calculates the amount of rise RT of the target temperature TT of the sensor cell 51 based on the degree of fall of the water repellency of the protective layer 60. The degree of fall of the water repellency of the protective layer 60 is judged by the judging part 80c. The heater control part 80b increases the amount of rise RT if the degree of fall of the water repellency of the protective layer 60 is relatively large compared to if the degree of fall of the water repellency of the protective layer 60 is relatively small. For example, the heater control part 80b uses a map such as shown in FIG. 19 to calculate the amount of rise RT.

Next, at step S603, the heater control part 80b rises the target temperature TT. Specifically, the heater control part 80b makes the value of the amount of rise RT calculated at step S602 added to the current target temperature TT the new target temperature TT. The initial value of the target temperature TT is a temperature of the lowest temperature where the Leidenfrost phenomenon occurs at the outer surface of the protective layer 60 or is more and is, for example, 400° C. or more. Further, the target temperature TT is returned to the initial value when the ignition switch of the vehicle carrying the internal combustion engine 1 is turned off or the internal combustion engine 1 is stopped. Note that, the initial value of the target temperature TT may be set to a temperature higher than the operating temperature of the sensor cell 51, for example, 700° C. or more. The operating temperature of the sensor cell 51 is the activation temperature of the sensor cell 51 or more and is, for example, 600° C. to 650° C.

Next, at step S604, the heater control part 80b sets the sensor abnormality flag Fsa to zero. After step S604, the present control routine is ended.

On the other hand, if at step S601 it is judged that the sensor abnormality flag Fsa has been set to zero, the present control routine is ended. In this case, the target temperature TT is maintained at the current target temperature.

Note that, in the present control routine, step S602 may be omitted. In this case, the amount of rise RT used at step S603 is made a predetermined value, for example, 50° C. to 100° C.

<Seventh Embodiment>

The configuration and control of the control device of an exhaust sensor according to a seventh embodiment are basically similar to the configuration and control of the control device of an exhaust sensor according to the sixth embodiment except for the points explained below. For this reason, below, the seventh embodiment of the present invention will be explained centered on the parts different from the sixth embodiment.

In the seventh embodiment, in the same way as the fifth embodiment, the control device of an exhaust sensor is further provided with an exhaust pipe temperature estimating part 80e. As explained above, when the temperature of the exhaust pipe 27 reaches the dew point temperature of water, new condensed water is not generated in the exhaust passage. For this reason, after the temperature of the exhaust pipe 27 reaches the dew point temperature of water, there is little possibility of the protective layer 60 being covered with water. For this reason, in the seventh embodiment, after the temperature of the exhaust pipe 27 estimated by the exhaust pipe temperature estimating part 80e reaches a predetermined temperature of the dew point temperature or more, the judging part 80c does not judge whether the water repellency of the protective layer 60 is falling. The heater control part 80b sets the target temperature of the sensor cell 51 to a predetermined operating temperature. The operating temperature of the sensor cell 51 is the activation temperature of the sensor cell 51 or more and is, for example, 600° C. to 650° C. Due to this, it is possible to suppress increase in the power consumption of the heater 55 due to maintaining the target temperature of the sensor cell 51 at a temperature higher than the operating temperature.

<Explanation of Control Using Time Chart>

Figure 22:
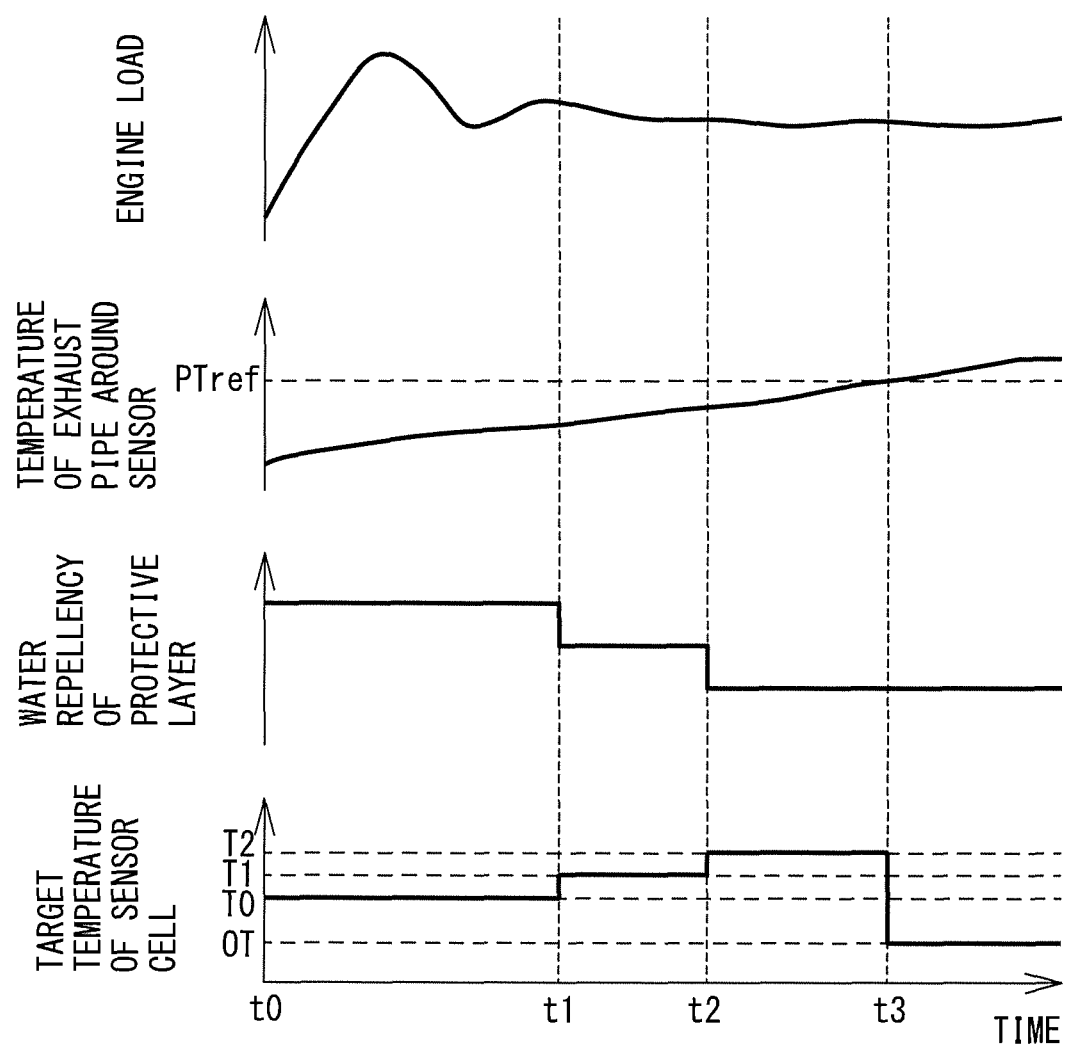
FIG. 22 is a schematic time chart of an engine load, temperature of an exhaust pipe around a sensor, water repellency of the protective layer, and target temperature of a sensor cell after making the internal combustion engine start up.

Below, referring to the time chart of FIG. 22, the control performed by the control device of an exhaust sensor in the seventh embodiment will be specifically explained. FIG. 22 is a schematic time chart of the engine load, the temperature of the exhaust pipe 27 (the temperature of the exhaust pipe around the sensor), the water repellency of the protective layer, and the target temperature of the sensor cell 51 after making the internal combustion engine start up. In the illustrated example, the temperature of the exhaust pipe 27 is calculated from the output of the exhaust temperature sensor 105.

In the illustrated example, at the time t0, the internal combustion engine 1 is started up. When the internal combustion engine 1 is started up, the target temperature of the sensor cell 51 is set to the initial temperature T0. The initial temperature T is the temperature of the lowest temperature where the Leidenfrost phenomenon occurs at the outer surface of the protective layer 60 or becomes more and is, for example, 750° C.

In the illustrated example, at the time t1, it is judged that the water repellency of the protective layer 60 is falling. For this reason, at the time t1, the target temperature of the sensor cell 51 is risen from the initial temperature T0 to the first temperature T1. The first temperature T1 is the temperature at which the outer surface of the protective layer 60 becomes the combustion temperature of soot or more and is, for example, 800° C.

Further, at the time t2, it is judged that the water repellency of the protective layer 60 has again fallen. For this reason, at the time t2, the target temperature of the sensor cell 51 is risen from the first temperature T1 to the second temperature T2. The second temperature T2 is for example 850° C.

After the time t2, at the time t3, the temperature of the exhaust pipe 27 reaches a predetermined temperature PTref of the dew point temperature or more. For this reason, at the time t3, the target temperature of the sensor cell 51 is set to the operating temperature OT. The predetermined temperature PTref is, for example, the dew point temperature (54° C.), while the operating temperature OT is, for example, 650° C.

<Processing for Setting Target Temperature>

Figure 23:
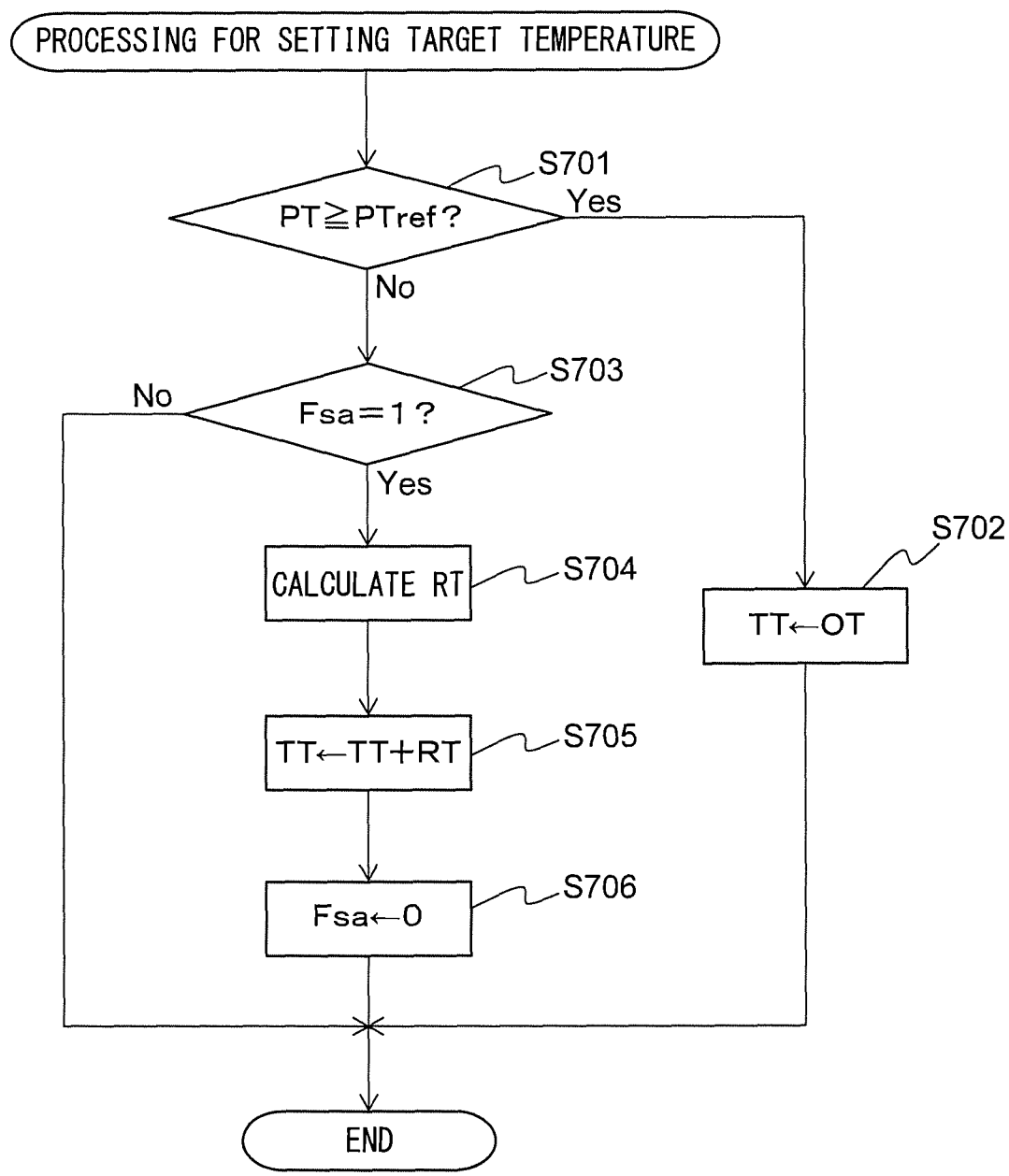
FIG. 23 is a flow chart showing a control routine of processing for setting a target temperature in the seventh embodiment of the present invention.

FIG. 23 is a flow chart showing the control routine of processing for setting a target temperature in the seventh embodiment of the present invention. The present control routine is repeatedly performed by the ECU 80 at predetermined time intervals after the startup of the internal combustion engine 1.

First, at step S701, the heater control part 80b judges whether the temperature PT of the exhaust pipe 27 estimated by the exhaust pipe temperature estimating part 80e is a predetermined temperature PTref of the dew point temperature or more or is more. The predetermined temperature PTref is, for example, the dew point (54° C.) or boiling point of water (100° C.). If at step S701 it is judged that the temperature PT of the exhaust pipe 27 is the predetermined temperature PTref or more, the present control routine proceeds to step S702.

At step S702, the heater control part 80b sets target temperature TT of the sensor cell 51 to the operating temperature OT. The operating temperature OT is the activation temperature of the sensor cell 51 or more and is, for example 600° C. to 650° C. After step S702, the present control routine is ended.

On the other hand, if at step S701 it is judged that the temperature PT of the exhaust pipe 27 is less than the predetermined temperature PTref, the present control routine proceeds to step S703. Step S703 to step S706 are similar to step S601 to step S604 in FIG. 21, so explanations will be omitted.

Note that, in the present control routine, step S704 may be omitted. In this case, the amount of rise RT used at step S705 is made a predetermined value, for example, is 50° C. to 100° C.

<Eighth Embodiment>

The configuration and control of the control device of an exhaust sensor according to an eighth embodiment are basically similar to the configuration and control of the control device of an exhaust sensor according to the sixth and seventh embodiments except for the points explained below. For this reason, below, the eighth embodiment of the present invention will be explained centered on the parts different from the sixth and seventh embodiments.

In the eighth embodiment, if the judging part 80c judges that the water repellency of the protective layer 60 is falling, the heater control part 80b rises the target temperature of the sensor cell 51 so that the temperature of the outer surface of the protective layer 60 becomes the combustion temperature of soot or more. If, in the period from when rising the target temperature to when the internal combustion engine 1 stops, a fall in the water repellency of the protective layer 60 is not again detected, there is a possibility that removal of the soot enabled the water repellency of the protective layer 60 to recover. For this reason, in the eighth embodiment, if the judging part 80c does not judge the water repellency of the protective layer 60 has again fallen in the period from when first rising the target temperature after the startup of the internal combustion engine 1 to when the internal combustion engine 1 stops, the heater control part 80b returns the target temperature after restart of the internal combustion engine 1 to the value before the rise. Due to this, it is possible to suppress an increase in the power consumption of the heater 55 due to rising the target temperature over a long period of time.

On the other hand, if a fall in the water repellency of the protective layer 60 is again detected in the period from when rising the target temperature to when the internal combustion engine 1 stops, the water repellency of the protective layer may permanently fall. For this reason, in the eighth embodiment, if the judging part 80c judges that the water repellency of the protective layer 60 has again fallen in the period from when first rising the target temperature after the startup of the internal combustion engine 1 to when the internal combustion engine 1 stops, the heater control part 80b further rises the target temperature and maintains the target temperature after restart of the internal combustion engine 1 at the value after the rise. Due to this, even after restart of the internal combustion engine 1, due to the Leidenfrost phenomenon, it is possible to effectively prevent the element of the air-fuel ratio sensor 10 from cracking.

In this regard, there is an upper limit to the temperature of the sensor cell 51 able to be controlled by the heater 55. However, if a fall in the water repellency of the protective layer 60 causes the target temperature of the sensor cell 51 to be made to rise a plurality of times, the target temperature will sometimes exceed the upper limit temperature. Further, if the temperature of the protective layer 60 is a high temperature, when water penetrates the protective layer 60, the thermal shock given to the protective layer 60 and element body 50 becomes larger. For this reason, if a fall in the water repellency of the protective layer 60 makes it difficult for the Leidenfrost phenomenon to occur at the outer surface of the protective layer 60, it is preferable to maintain the temperature of the outer surface of the protective layer 60 at a low temperature to prevent the element of the air-fuel ratio sensor 10 from cracking due to coverage by water.

For this reason, in the eighth embodiment, the heater control part 80b turns the heater 55 off if rising the target temperature of the sensor cell 51 a plurality of times causes the target temperature to exceed a predetermined upper limit temperature. The upper limit temperature is predetermined from the configuration of the sensor element 12 etc. and is for example 900° C. Note that, if turning the heater 55 off, the temperature of the sensor cell 51 becomes less than the activation temperature and accurate detection of the air-fuel ratio becomes difficult. For this reason, while the heater 55 is turned off, the air-fuel ratio sensor 10 does not detect the air-fuel ratio.

Further, in the eighth embodiment, in the same way as the seventh embodiment, the heater control part 80b sets the target temperature of the sensor cell 51 to a predetermined operating temperature after the temperature of the exhaust pipe 27 estimated by the exhaust pipe temperature estimating part 80e reaches a predetermined temperature of the dew point temperature or more. Due to this, the air-fuel ratio sensor 10 can be used to detect the air-fuel ratio after the amount of condensed water inside the exhaust passage becomes smaller.

Note that, the heater control part 80b may set the target temperature of the sensor cell 51 to a temperature of less than the lowest temperature at which the Leidenfrost phenomenon occurs at the outer surface of the protective layer 60 if rising target temperature of the sensor cell 51 a plurality of times causes the target temperature to exceed a predetermined upper limit temperature. For example, the heater control part 80b sets the target temperature of the sensor cell 51 to 300° C. Due to this, compared with when turning the heater 55 off, after the temperature of the exhaust pipe 27 reaches a predetermined temperature of the dew point temperature or more, the target temperature can be made to quickly rise to the operating temperature, so it is possible to detect the air-fuel ratio using the air-fuel ratio sensor 10 early.

<Control Routine of Processing for Judging Abnormality>

Figure 24:
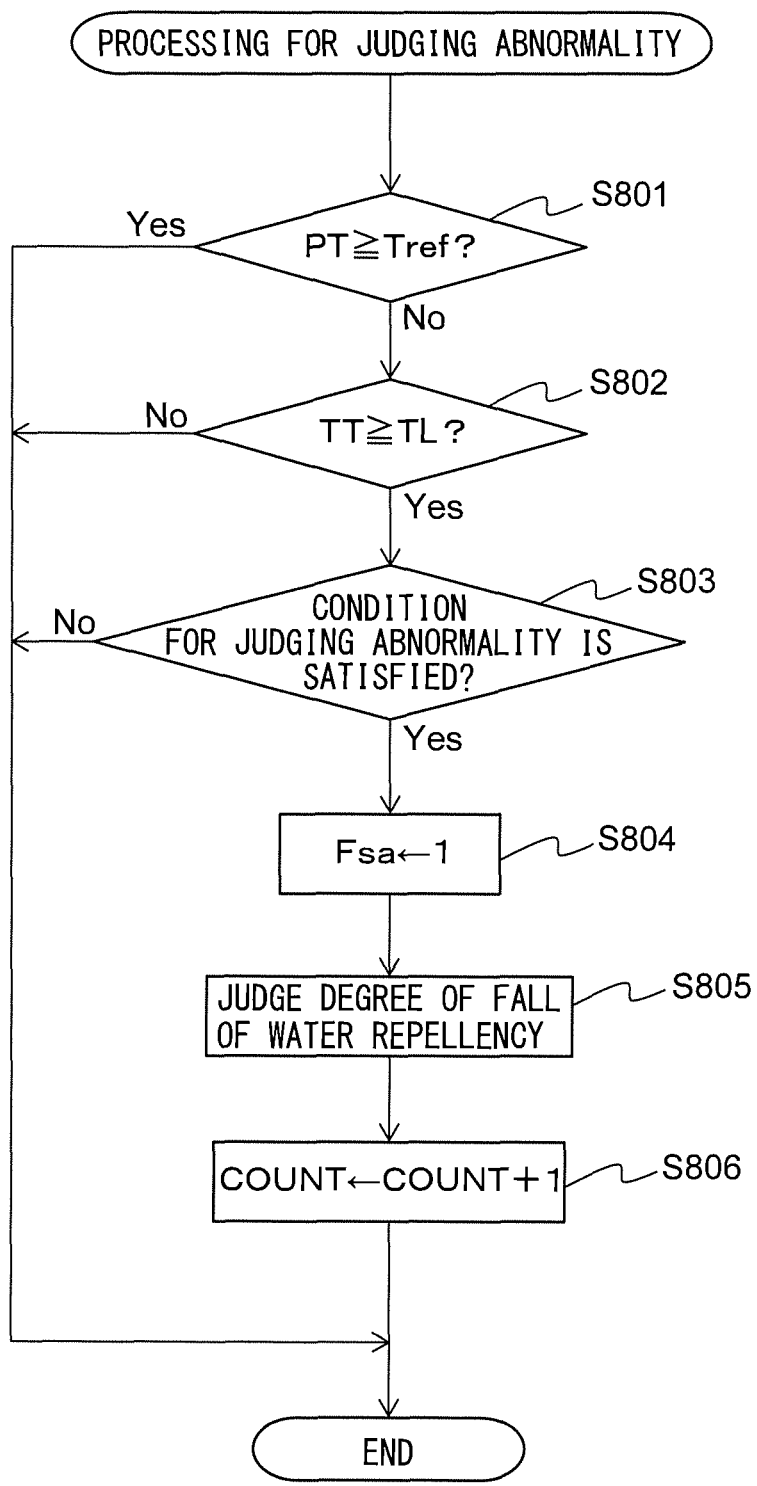
FIG. 24 is a flow chart showing a control routine of processing for judging abnormality in the eighth embodiment of the present invention.

FIG. 24 is a flow chart showing a control routine of processing for judging abnormality in the eighth embodiment of the present invention. The illustrated control routine is repeatedly performed by the ECU 80 at predetermined time intervals after the startup of the internal combustion engine 1. Step S801 to step S804 in FIG. 24 are similar to step S501 to step S504 in FIG. 18, so explanations will be omitted.

The present control routine proceeds to step S805 after step S804. At step S805, in the same way as step S206 in FIG. 8, the judging part 80c the degree of fall of the water repellency of the protective layer 60.

At step S806, the judging part 80c updates the number of times of judgment COUNT. Specifically, the judging part 80c makes the value of the current number of times of judgment COUNT plus 1 the new number of times of judgment COUNT. The number of times of judgment COUNT shows the number of times it is judged that the water repellency of the protective layer 60 is falling from when the internal combustion engine 1 is started to when it is stopped. The initial value of the number of times of judgment COUNT is zero. Further, the number of times of judgment COUNT is made zero when the ignition switch of the vehicle carrying the internal combustion engine 1 is turned off or when the internal combustion engine 1 is stopped. After step S806, the present control routine is ended.

<Processing for Setting Target Temperature>

Figure 25:
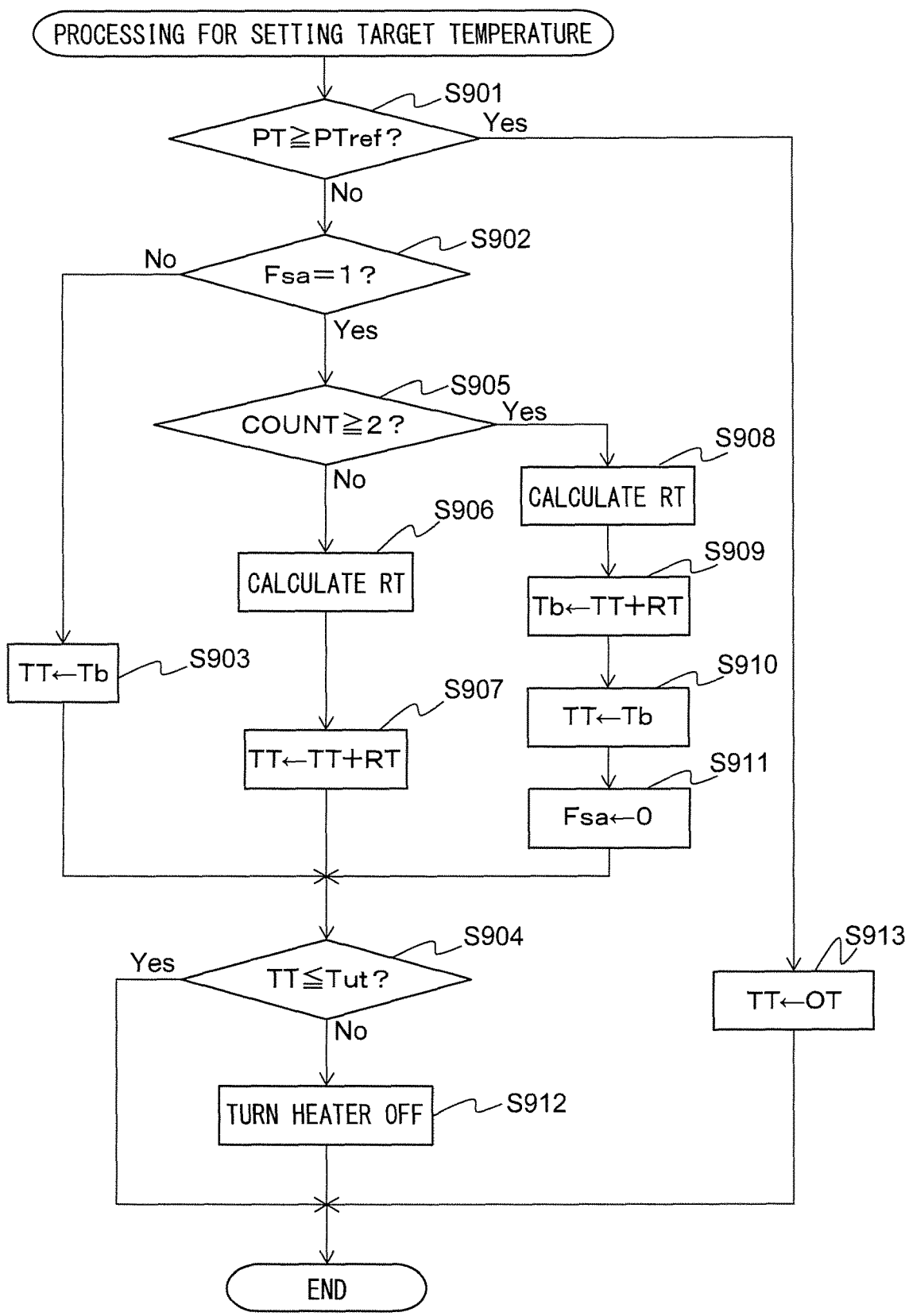
FIG. 25 is a flow chart showing a control routine of processing for setting a target temperature in the eighth embodiment of the present invention.

FIG. 25 is a flow chart showing the control routine of processing for setting a target temperature in the eighth embodiment of the present invention. The present control routine is performed repeatedly by the ECU 80 at predetermined time intervals after the startup of the internal combustion engine 1.

First, at step S901, the heater control part 80b judges whether the temperature PT of the exhaust pipe 27 estimated by the exhaust pipe temperature estimating part 80e is a predetermined temperature PTref, which is the dew point temperature or more, or more. The predetermined temperature PTref is for example the dew point (54° C.) or boiling point of water (100° C.). If at step S901 it is judged that the temperature PT of the exhaust pipe 27 is less than a predetermined temperature PTref, the present control routine proceeds to step S902.

At step S902, the heater control part 80b judges whether the sensor abnormality flag Fsa has been set to "1". If it is judged that the sensor abnormality flag Fsa has been set to zero, the present control routine proceeds to step S903.

At step S903, the heater control part 80b sets the target temperature TT to the base temperature Tb. The initial value of the base temperature Tb is the lowest temperature at which the Leidenfrost phenomenon occurs at the outer surface of the protective layer 60 or more and, for example, is 400° C. or more. Note that, the initial value of the base temperature Tb may be set to a temperature higher than the operating temperature of the sensor cell 51, for example, a temperature of 700° C. or more.

Next, at step S904, the heater control part 80b judges whether the target temperature TT set at step S903 is the upper limit temperature Tut or less. The upper limit temperature Tut is for example 900° C. If it is judged at step S904 that the target temperature TT is the upper limit temperature Tut or less, the present control routine is ended.

On the other hand, if at step S902 it is judged that the sensor abnormality flag Fsa is set to "1", the present control routine proceeds to step S905. At step S905, the heater control part 80b judges whether the number of times of judgment COUNT is 2 or more. The number of times of judgment COUNT is updated at step S806 of FIG. 24. If at step S905 it is judged that the number of times of judgment COUNT is "1", the present control routine proceeds to step S906.

At step S906, in the same way as step S602 of FIG. 21, the target temperature TT of the heater control part 80b calculates the amount of rise RT of the sensor cell 51 based on the degree of fall of the water repellency of the protective layer 60. Next, at step S907, the heater control part 80b rises the target temperature TT. Specifically, the heater control part 80b makes the value of the amount of rise RT calculated at step S906 added to the current target temperature TT the new target temperature TT.

Next, at step S904, the heater control part 80b judges whether the target temperature TT set at step S907 is the upper limit temperature Tut or less. If it is judged that the target temperature TT is the upper limit temperature Tut or less, the present control routine is ended.

On the other hand, if at step S905 it is judged that the number of times of judgment COUNT is 2 or more, the present control routine proceeds to step S908. In this case, it is judged that the water repellency of the protective layer 60 has again fallen in the period from when rising the target temperature TT at step S907, to when the internal combustion engine 1 stops.

At step S908, in the same way as step S602 of FIG. 21, the heater control part 80b calculates the amount of rise RT of the base temperature Tb based on the degree of fall of the water repellency of the protective layer 60. Next, at step S909, the heater control part 80b rises the base temperature Tb. Specifically, the heater control part 80b makes the value of the amount of rise RT calculated at step S908 added to the current base temperature Tb the new base temperature Tb. The base temperature Tb is stored in the RAM 83 of the ECU 80. The updated value is held even after the ignition switch is turned off.

Next, at step S910, the heater control part 80b rises the target temperature TT. Specifically, the heater control part 80b sets the target temperature TT to the base temperature Tb updated at step S909. Next, at step S911, the heater control part 80b sets the sensor abnormality flag Fsa to zero.

Next, at step S1004, the heater control part 80b judges at step S1007, the target temperature TT set at step S1010 is the upper limit temperature Tut or less. If it is judged that the target temperature TT is the upper limit temperature Tut or less, the present control routine is ended.

On the other hand, if at step S904 it is judged that the target temperature TT set at step S903, step S907, or step S910 is higher than the upper limit temperature Tut, the present control routine proceeds to step S912. In this case, it is difficult to cause the Leidenfrost phenomenon to occur at the outer surface of the protective layer 60 and thereby prevent the element of the air-fuel ratio sensor 10 from cracking, so at step S1012, the heater control part 80b turns the heater 55 off. After step S912, the present control routine is ended.

Further, if it is judged at step S901 that the temperature PT of the exhaust pipe 27 is a predetermined temperature PTref or more, the present control routine proceeds to step S913. At step S913, the heater control part 80b sets the target temperature TT of the sensor cell 51 to the operating temperature OT. The operating temperature OT is the activation temperature of the sensor cell 51 or more and, for example 600° C. to 650° C. After step S913, the present control routine is ended.

Note that, at step S912, the heater control part 80b may set the target temperature of the sensor cell 51 to a temperature (for example 300° C.) less than the lowest temperature at which the Leidenfrost phenomenon occurs at the outer surface of the protective layer 60. Further, step S805 of FIG. 24 and step S906 and step S908 of FIG. 25 may be omitted. In this case, the amount of rise RT used at step S907 and step S909 is made a predetermined value, for example, 50° C. to 100° C. Further, the amount of rise RT used at step S907 and the amount of rise RT used at step S909 may be different values.

Above, preferred embodiments according to the present invention were explained, but the present invention is not limited to these embodiments. Various corrections and changes may be made within the language of the claims. For example, the exhaust sensor controlled by the control device of the exhaust sensor may be an oxygen sensor detecting if the air-fuel ratio of the exhaust gas is rich or lean by detecting the oxygen in the exhaust gas. Further, the exhaust sensor may be a nitrogen oxide sensor ($NO_X$ sensor) detecting the concentration of nitrogen oxides ($NO_X$) in the exhaust gas, a sulfur oxide sensor ($SO_X$ sensor) detecting the concentration of sulfur oxides ($SO_X$) in the exhaust gas, etc.

Further, the element body of the exhaust sensor may be provided with another electrochemical cell in addition to the sensor cell. The other electrochemical cell is, for example, a pump cell discharging the oxygen in the measured gas from the measured gas chamber, a monitor cell detecting the concentration of a specific component in the measured gas, etc. In this case, the heater control part may set the target temperature of the pump cell or monitor cell and control the heater so that the temperature of the pump cell or monitor cell becomes the target temperature. The temperature of the pump cell or monitor cell is calculated by its impedance, etc.

Further, the above-mentioned embodiments can be freely combined and carried out. For example, after step S308 of FIG. 10, step S411 of FIG. 13, step S414 of FIG. 14, or step S504 of FIG. 18, step S206 of FIG. 8 may be performed.

REFERENCE SIGNS LIST 1. internal combustion engine
10. exhaust sensor (air-fuel ratio sensor)
12. sensor element
50. element body
51. sensor cell
55. heater
60. protective layer
80. electronic control unit (ECU)
80a. cell temperature detecting part
80b. heater control part
80c. judging part
80d. output detecting part
80e. exhaust pipe temperature estimating part

The invention claimed is:

1. A control device of an exhaust sensor controlling an exhaust sensor arranged in an exhaust passage of an internal combustion engine and detecting a specific component in exhaust gas, wherein
    the exhaust sensor comprises an element body provided with an electrochemical cell, a protective layer formed on an outer surface of the element body and comprised of a porous ceramic, and a heater heating the element body and the protective layer,
    the control device comprises a cell temperature detecting part configured to detect a temperature of the electrochemical cell, a heater control part configured to set a target temperature of the electrochemical cell and control the heater so that a temperature of the electrochemical cell becomes the target temperature, and a judging part configured to judge whether a water repellency of the protective layer is falling when the heater control part sets the target temperature to a temperature of a lowest temperature at which a Leidenfrost phenomenon occurs at an outer surface of the protective layer or more, and
    the judging part is configured to judge that the water repellency of the protective layer is falling if a condition for judging abnormality is satisfied, the condition for judging abnormality including a temperature of the electrochemical cell detected by the cell temperature detecting part falling from the target temperature and a speed of fall of the temperature being faster than a speed of fall of the temperature of the electrochemical cell when the heater is turned off.

2. The control device of an exhaust sensor according to claim 1, wherein the condition for judging abnormality includes an amount of fall of the temperature of the electrochemical cell from the target temperature being a predetermined amount or more.

3. The control device of an exhaust sensor according to claim 1, wherein the condition for judging abnormality includes a temperature of the electrochemical cell falling from the target temperature, then rising to the target temperature, and a time period from when the temperature of the electrochemical cell falls from the target temperature to when it rises to the target temperature being shorter than an ignition period in the internal combustion engine.

4. The control device of an exhaust sensor according to claim 1, wherein the condition for judging abnormality includes a temperature of the electrochemical cell falling from the target temperature, then rising to the target temperature, and a speed of fall and a speed of rise of the temperature being a predetermined speed or more.

5. The control device of an exhaust sensor according to claim 1, wherein the condition for judging abnormality includes a temperature of the electrochemical cell falling from the target temperature, then rising to the target temperature, and a speed of fall of the temperature being faster than a speed of rise of the temperature.

6. The control device of an exhaust sensor according to claim 1, further comprising an output detecting part configured to detect an output of the exhaust sensor, wherein
the condition for judging abnormality includes an absolute value of the output of the exhaust sensor detected by the output detecting part falling from the value of a predetermined reference value or more when the temperature of the electrochemical cell falling from the target temperature.

7. The control device of an exhaust sensor according to claim 6, wherein the condition for judging abnormality includes an amount of fall of the absolute value of the output of the exhaust sensor from the value of the reference value or more being a predetermined amount or more.

8. The control device of an exhaust sensor according to claim 6, wherein the condition for judging abnormality includes the absolute value of the output of the exhaust sensor falling from the value of the reference value or more, then rising to the value of the reference value or more, and a time period from when the absolute value of the output of the exhaust sensor falls from the value of the reference value or more to when it rises to the value of the reference value or more being shorter than an ignition period in the internal combustion engine.

9. The control device of an exhaust sensor according to claim 6, wherein the condition for judging abnormality includes the absolute value of the output of the exhaust sensor falling from the value of the reference value or more, then rising to the value of the reference value or more, and a speed of fall and speed of rise of the absolute value of the output being a predetermined speed or more.

10. The control device of an exhaust sensor according to claim 6, wherein the condition for judging abnormality includes the absolute value of the output of the exhaust sensor falling from the value of the reference value or more, then rising to the value of the reference value or more, and a speed of fall of the absolute value of the output being faster than a speed of rise of the absolute value of the output.

11. The control device of an exhaust sensor according to claim 1, further comprising an output detecting part configured to detect an output of the exhaust sensor, wherein
the condition for judging abnormality includes the output of the exhaust sensor detected by the output detecting part rising from a value in a predetermined near zero region when the temperature of the electrochemical cell falls.

12. The control device of an exhaust sensor according to claim 11, wherein the condition for judging abnormality includes the output of the exhaust sensor rising from the value in the near zero region then falling to the value in the near zero region, and a time period from when the output of the exhaust sensor rises from the value in the near zero region to when it falls to the value in the near zero region being shorter than an ignition period in the internal combustion engine.

13. The control device of an exhaust sensor according to claim 1, further comprising an exhaust pipe temperature estimating part configured to estimate a temperature of the exhaust pipe around the exhaust sensor, wherein
the judging part is configured not to judge whether the water repellency of the protective layer is falling after the temperature of the exhaust pipe estimated by the exhaust pipe temperature estimating part reaches a predetermined temperature of a dew point temperature or more.

14. The control device of an exhaust sensor according to claim 1, wherein the judging part is configured to judge a degree of fall of the water repellency of the protective layer, and judge that a degree of fall of the water repellency of the protective layer is larger the larger an amount of fall of the temperature of the electrochemical cell from the target temperature when the temperature falls from the target temperature at a speed faster than the speed of fall of the temperature of the electrochemical cell when the heater is turned off.

15. The control device of an exhaust sensor according to claim 1, wherein the heater control part is configured to rise the target temperature when the judging part judges that the water repellency of the protective layer is falling.

16. The control device of an exhaust sensor according to claim 14, wherein the heater control part is configured to rise the target temperature when the judging part judges that the water repellency of the protective layer is falling, and makes an amount of rise of the target temperature larger if a degree of fall of water repellency of the protective layer is relatively large compared with if the degree of fall of water repellency of the protective layer is relatively small.

* * * * *